(12) United States Patent
Chung et al.

(10) Patent No.: US 9,474,777 B2
(45) Date of Patent: Oct. 25, 2016

(54) PLANT EXTRACT AND THE PROCESS FOR TREATING HEPATIC FIBROSIS AND LIVER CANCER

(71) Applicant: Development Center for Biotechnology, New Taipei (TW)

(72) Inventors: Yuh-Shan Chung, New Taipei (TW); Ma-Li Siu, New Taipei (TW); Tzung-Hsien Lai, New Taipei (TW); Szu-Chien Yeh, New Taipei (TW)

(73) Assignee: Development Center for Biotechnology, New Taipei (TW)

( * ) Notice: Subject to any disclaimer, the term of this patent is extended or adjusted under 35 U.S.C. 154(b) by 4 days.

(21) Appl. No.: 14/144,264

(22) Filed: Dec. 30, 2013

(65) Prior Publication Data
US 2015/0182572 A1    Jul. 2, 2015

(51) Int. Cl.
*A61K 36/00* (2006.01)
*A61K 36/41* (2006.01)

(52) U.S. Cl.
CPC ............ *A61K 36/41* (2013.01); *A61K 2236/00* (2013.01)

(58) Field of Classification Search
None
See application file for complete search history.

(56) References Cited

U.S. PATENT DOCUMENTS

| 7,364,758 | B2 | 4/2008 | Hsu | |
|---|---|---|---|---|
| 2012/0259004 | A1* | 10/2012 | Huang | A61K 36/41 514/456 |

FOREIGN PATENT DOCUMENTS

| CN | 102521959 A | 6/2012 |
|---|---|---|
| CN | 103269706 A | 8/2013 |
| TW | 200516655 A | 1/2000 |
| TW | 2012-19047 A | 5/2012 |
| WO | 2006/024143 A1 | 3/2006 |
| WO | 2012/041256 A1 | 4/2012 |

OTHER PUBLICATIONS

Wickramasinghe, Tangential flow microfiltration and ultrafiltration for human influenza A virus concentration and purification. Biotechnology and bioengineering, (Oct. 20, 2005) vol. 92, No. 2, pp. 199-208.*
Extended European Search Report dated Jun. 12, 2014, in corresponding European Patent Application No. 13199870.0-1456 (7 pages).
Su, Li-Jen, et al., "Graptopetalum Paraguayense Ameliorates chemical-Induced Rat Hepatic Fibrosis In Vivo and Inactivates Stellate Cells and Kupffer Cells In Vitro"; Plos One, vol. 8, Issue 1, e53988; Jan. 15, 2013; XP55121097, DOI: 10.1371/journal.pone.0053988; pp. 1-13.
Duh, Pin-Der, et al., "Hepatoprotection of Graptopetalum paraguayense E. Walther on CCl4-induced liver damage and inflammation"; Journal of Ethnopharmacology, Elsevier Ireland Ltd., vol. 134, No. 2, Dec. 12, 2010; XP028162630, ISSN: 0378-8741, DOI: 10.1016/J.JEP.2010.12.029; pp. 379-385.
Lin Yu-Ling, et al., "Effects of Graptopetalum paraguayense consumption on serum lipid profiles and antioxidative status in hypercholesteremic subjects"; J. Sci. Food Agric., vol. 91, Issue 7; May 2011; doi: 10.1002/jsfa.4304; pp. 1230-1235 [Abstract only].
Kao, Tsung-Kuei, et al., "Graptopetalum paraguayense E. Walther Leaf Extracts Protect Against Brain Injury in Ischemic Rats"; Am. J. Chin. Med., vol. 38, Issue 3, (2010); doi: 10.1142/50192415X10008019; pp. 495-516 (Abstract only).
Dfficial Action dated Aug. 20, 2015, issued by the State Intellectual Property Office of The Peoples Republic of china in related Chinese Patent Application No. 103145524 (4 pages).

* cited by examiner

*Primary Examiner* — Qiuwen Mi
(74) *Attorney, Agent, or Firm* — Osha Liang LLP

(57) ABSTRACT

An extract of *Graptopetalum paraguayense* prepared by a method that includes: extracting a *Graptopetalum paraguayense* (GP) starting material with an alcoholic solvent to produce an alcoholic extract and a residue; separating the residue from the alcoholic extract; extracting the residue with an aqueous dimethyl sulfoxide (DMSO) solvent to produce a DMSO extract; subjecting the DMSO extract to ultrafiltration using a filter having a selected molecular weight cutoff; drying a fraction retained by the filter to obtain the extract of *Graptopetalum paraguayense*. Uses of an extract of *Graptopetalum paraguayense* for the treatment or prevention of liver fibrosis, hepatic cirrhosis, liver cancer, recurrence of liver fibrosis after surgery, or recurrence of liver cancer after surgery.

6 Claims, 24 Drawing Sheets

| m/z | charge | [M-H+] | M(Experiment) | [M-H+]- 分子式 | difference (ppm) | number | number | Oxygen number |
|---|---|---|---|---|---|---|---|---|
| 761.1367 | 1 | 761.1367 | 762.1445 | $C_{37}H_{29}O_{18}$ | 1.47 | 2 | 1 | |
| 929.1429 | 1 | 929.1429 | 930.1507 | $C_{44}H_{33}O_{23}$ | 1.73 | 2 | 2 | +1 |
| 684.1054 | 2 | 1369.2186 | 1370.2264 | $C_{66}H_{50}O_{33}$ | 2.16 | 3 | 3 | |
| 692.1028 | 2 | 1385.2134 | 1386.2212 | $C_{66}H_{50}O_{34}$ | 2.04 | 3 | 3 | +1 |
| 836.1347 | 2 | 1673.2772 | 1674.285 | $C_{81}H_{62}O_{40}$ | 1.95 | 4 | 3 | |
| 912.1401 | 2 | 1825.288 | 1826.2958 | $C_{88}H_{66}O_{44}$ | 1.7 | 4 | 4 | |
| 988.1623 | 2 | 1977.3324 | 1978.3402 | $C_{96}H_{74}O_{47}$ | 0.08 | 5 | 3 | |
| 1064.17 | 2 | 2129.3478 | 2130.3556 | $C_{103}H_{78}O_{51}$ | 2.16 | 5 | 4 | |
| 1132.1744 | 2 | 2265.3566 | 2266.3644 | $C_{110}H_{82}O_{54}$ | -1.16 | 5 | 5 | -1 |
| 1140.1735 | 2 | 2281.3548 | 2282.3626 | $C_{110}H_{82}O_{55}$ | 0.28 | 5 | 5 | |
| 1216.198 | 2 | 2433.4038 | 2434.4116 | $C_{118}H_{90}O_{58}$ | 0.94 | 6 | 4 | |
| 1292.2024 | 2 | 2585.4126 | 2586.4204 | $C_{125}H_{94}O_{62}$ | 0.05 | 6 | 5 | |
| 1368.2052 | 2 | 2737.4182 | 2738.426 | $C_{132}H_{98}O_{66}$ | -1.9 | 6 | 6 | |
| 962.8195 | 3 | 2889.4663 | 2890.4741 | $C_{140}H_{106}O_{69}$ | -1.54 | 7 | 5 | |
| 1013.4893 | 3 | 3041.4757 | 3042.4835 | $C_{147}H_{110}O_{73}$ | -1.98 | 7 | 6 | |
| 1064.1606 | 3 | 3193.4896 | 3194.4974 | $C_{154}H_{114}O_{77}$ | -0.96 | 7 | 7 | |
| 1165.5115 | 3 | 3497.5423 | 3498.5501 | $C_{169}H_{126}O_{84}$ | -2.48 | 8 | 7 | |
| 1216.1824 | 3 | 3649.555 | 3650.5628 | $C_{176}H_{130}O_{88}$ | -1.89 | 8 | 8 | |
| 1317.5331 | 3 | 3953.6071 | 3954.6149 | $C_{191}H_{142}O_{95}$ | -3.31 | 9 | 8 | |

Result Summary

| Test drugs | | MTT assay (IC$_{50}$) | | Western blot | |
|---|---|---|---|---|---|
| Source | Name | Mahlavu | Huh7 | AURK expression | CEP55 expression |
| YM (GP-P) | GP | ~250 | ~500 | ↓ | ↓ |
| DCB (GP-P) | GP-1 | ~250 | ~500 | ↓ | ↓ |
| YM (active fraction) | HH-F3 | ~25 | ~50 | ↓ | ↓ |
| DCB Different batches GP-T | GP-7-1 | ~50 | ~50 | ↓ | ↓ |
| | GP-8-1 | ~50 | ~50 | ↓ | ↓ |
| | GP-8-2 | ~50 | ~75 | ↓ | ↓ |
| | GP-8-3 | ~25 | ~75 | ↓ | ↓ |
| | GP-8-4 | ~50 | ~75 | ↓ | ↓ |
| | GP-8-4-1 | ~50 | ~75 | ↓ | ↓ |
| | GP-8-4-2 | ~50 | ~75 | ↓ | ↓ |
| | GP-9 | ~25 | ~50 | ↓ | ↓ |
| | GP-F20 | ~50 | 75-100 | ↓ | ↓ |
| | GP-F30 | ~100 | >100 | | |

↓ : down-regulation
↑ : up-regulation

FIG. 7C

AURKA/B: Aurora kinase A/B; CEP55: 55kDa centrosomal protein; PTEN: phosphatase and tensin homolog protein; α-SMA: alpha-smooth muscle actin;

| | normal | DEN | Sorafenib 30 mg/kg | GP-T 50 mg/kg | GP-T 150 mg/kg |
|---|---|---|---|---|---|
| Liver Cell Apoptosis | 0 | 2 | 2 | 2 | 1 |
| Nodular regeneration | 0 | 3.5 | 2 | 1.5 | 0 |
| Bile duct proliferation | 0 | 2 | 1.5 | 1 | 0 |
| Cystic formation | 0 | 2 | 1 | 0 | 0 |
| Proliferation of oval cells | 0 | 3 | 2 | 2 | 1.5 |
| Eosinophilic hepatoma | 0 | 2 | 1 | 0 | 0 |
| Number | 8 | 10 | 12 | 11 | 12 |

*: $p<0.5$ ; : $p<0.05$ ; *: $p<0.01$

*: $p<0.5$; : $p<0.05$; *: $p<0.01$

*: p<0.5 ; : p<0.05 ; *: p<0.01

PLANT EXTRACT AND THE PROCESS FOR TREATING HEPATIC FIBROSIS AND LIVER CANCER

FIELD OF THE INVENTION

The present invention relates to the field of active fractions of *Graptopetalum paraguayense*, particularly, extracts of *Graptopetalum paraguayense* and methods for their productions and their uses.

BACKGROUND OF INVENTION

*Graptopetalum paraguayense* (GP) are medicinal plants that look like lotus (rosette). However, their leaves are drought resistant. Therefore, they are referred to as stone lotus or *Cyperus alternifolius*. They belong to *Crassulaceae sinocrassula*. They are perennial succulent plants. The plant is smooth and thick. The color is powdery white and the leaves aggregates on top of the stem; the leaves are without stems with an inverted egg shape arranged like a lotus flower (rosette), which gives it the name stone lotus. The plants occasionally bloom small white flowers in the spring and fall. GP may be cultivated for ornamental purposes or for medicinal use.

GP is considered to have potentially beneficial effects in alleviating hepatic disorders, lowering blood pressure, whitening skin, relieving pain and infections, inhibiting inflammation, and improving brain function.

GP is rich in ash materials and various nutrients, such as dietary fibers, sodium, calcium, potassium, magnesium, iron, vitamins C, B1, B2, B6, folic acid, nicotinic acid, and β-carotene. It is an edible plant. Its pharmacological activities include rejuvenation of liver cells, improving immune functions, alleviating fragile blood vessel and abnormal permeability, preventing various diseases, such as high blood pressure, arteriosclerosis, chronic hepatitis, and liver cirrhosis.

GP was investigated as food supplement for the control of lipid levels in people with hyperlipoidemia (J Sci Food Agric. 2011 May; 91(7):1230-5). In a clinical trial, 18 hyperlipoidemia subjects were given 100 g of fresh GP daily. After eight weeks, the test subjects were assessed for their serum indicators and blood analysis. The results show that GP uptake can substantially increase the antioxidant activities in the bodies (the levels of ascorbic acid and α-tocopherol in blood increased and the level of malondialdehyde decreased; glutathione concentration increased in red blood cells; glutathione peroxidase and catalase activities also increased). It was found that a product from ethyl acetate re-extraction of a 50% ethanol extract of GP has neuroprotective effects in rats with stroke (Am. J. Chin. Med., 2010, 38(3): 495-516).

Researchers in Taiwan also found that GP can inhibit hepatitis and hepatic fibrosis that is induced by dimethylnitrosamine (DMN) or carbon tetrachloride ($CCl_4$). In in vitro cell studies of hepatic fibrosis, it was found: (1) GP-W could inhibit the growth of hepatic stellate cells (HSC) or induce their apoptosis; (2) GP extracts could delay the aging of Kupffer cells, as compared to a control group; (3) GP extracts could inhibit lipopolysaccharide (LPS)-induced inflammation in Kupffer cells, resulting in lower expression of TNF-α and IL-6.

GP active ingredients have been subjects of several patent applications, including TW patent application publication No. TW200616655 (Pharmaceutical use of *Graptopetalum* and related plants), which corresponds to U.S. Pat. No. 7,364,758; U.S. patent application Publication No. US 2012/259004 A1 (Anti-cancer extract and compounds); Taiwan patent application publication No. TW201219047 (Anti-cancer extract and compounds); and Chinese patent application publication No. CN103269706 (Anti-cancer extract and compounds).

In U.S. Pat. No. 7,364,758 ("Pharmaceutical use of *Graptopetalum* and related plants"), GP flower extracts were obtained using water, ethanol, acetone, methanol, or a mixture thereof as a solvent, while the Pharmaceutical use is for the treatment or prevention of a disease selected from the group consisting of liver inflammation, hepatic steatosis, liver fibrosis, hepatocirrhosis, and hepatitis B. The extracts disclosed in the '758 patent were obtained with polar solvents.

The patent applications "Anti-cancer extract and compounds" mainly concern DMSO extracts of *Graptopetalum* sp. *Rhodiola* sp. or *Echeveria* sp. In these applications, the DMSO extracts were further purified with Sephadex LH20 column chromatography to isolate HH-F3, a proanthocyanidin compound with a molecule weight of about 18 kD. However, the use of column chromatography makes it impractical to have large scale productions. In addition, column elution requires a large amount of organic solvents, and the necessary processes to concentrate the fractions are also costly.

While these prior art disclosures show that GP extracts have beneficial medicinal uses and the prior art methods can produce OP extracts with good activities, there is still a need for better methods for the preparation of GP extracts, particularly methods that are suitable for economical, large scale productions.

SUMMARY OF INVENTION

Embodiments of the invention relate to new pharmaceuticals, i.e., extracts of GP active ingredients, and methods for their preparations and uses. In accordance with embodiments of the invention, GP extracts may be obtained by organic solvent extraction followed by purification using a tangential flow filtration (TFF) system. The TFF purification method relies on dialysis (ultrafiltration), together with the use of specific dialysis solution, to prepare active plant extracts. This approach, as compared with column purification, is more suitable for large scale productions, and it is more economical because it avoids the costs of large volumes of solvents and costs associated with concentration of solvents when using column chromatography.

Some embodiments of the invention relate to use of chemical preparation methods to isolate and purify and natural products for use in the protection of liver function and prevention of liver damages, liver fibrosis, hepatic cirrhosis, and in the treatment of liver cancers.

In accordance with embodiments of this invention, a method for preparing active extract fraction may include extraction with methanol to remove soluble component, and the residues are then extracted with 30% DMSO to obtain the active extracts. The active extracts are then subjected to ultrafiltration, such as tangential flow filtration (TFF), using a suitable molecular weight cutoff membrane (e.g., 5 kD cutoff). The active fraction retained by the filtration membrane is concentrated to obtain a partially purified active fraction, which may be used to protect liver functions, and to prevent and treat liver damages, liver fibrosis, liver (hepatic) cirrhosis, recurrence of liver fibrosis after surgery, and recurrence of liver cancer after surgery.

The active fractions contain polymeric tannins, that comprise one or more phenolic compounds selected from the group consisting of: (−)-Epicatechin, (−)-Epigallocatechin, (−)-Epigallocatechin gallate, (−)-Epicatechin-3-O-gallate, (−)-Epigallocatechin gallate, and one or more sugars selected from the group consisting of arabinose, galactose, glucose, rhamnose, glucuronic acid, and galacturonic acid, etc.

In accordance with some embodiments of the invention, the main components include polymeric tannins that are composed of compounds having (−)-Epigallocatechin gallate as the terminal units, or compounds having (−)-Epigallocatechin gallateas as the main units.

In one aspect, embodiments of the invention relate to methods for the preparation of an extract of *Graptopetalum paraguayense*. A method in accordance with one embodiment of the invention may include the following steps: extracting a *Graptopetalum paraguayense* (GP) starting material with an alcoholic solvent (e.g., methanol or ethanol) to produce an alcoholic extract and a residue; separating the residue from the alcoholic extract; extracting the residue with an aqueous dimethyl sulfoxide (DMSO) solvent to produce a DMSO extract; subjecting the DMSO extract to ultrafiltration using a filter having a selected molecular weight cutoff; drying a fraction retained by the filter to obtain the extract of *Graptopetalum paraguayense*. The GP starting may be a powder of leaves of GP. The aqueous dimethyl sulfoxide (DMSO) solvent contains about 30% DMSO. The DMSO extract was diluted with water to about 10% DMSO prior to ultrafiltration. The ultrafiltration may be performed using a tangential flow filtration system. The selected molecular weight cutoff may be about 5 kD. The method may further comprise filtering the DMSO extract prior to ultrafiltration.

In another aspect of the invention, embodiments of the invention relate to uses of an extract of *Graptopetalum paraguayense* for the treatment or prevention of liver fibrosis, hepatic cirrhosis, liver cancer, recurrence of liver fibrosis after surgery, or recurrence of liver cancer after surgery.

Other aspects of the invention will be apparent in view of the attached drawings and the following description.

BRIEF DESCRIPTION OF THE DRAWINGS

FIG. 7C shows summary results of tests of FIG. 7A and FIG. 7B.

DETAILED DESCRIPTION OF THE INVENTION

Figure 1:
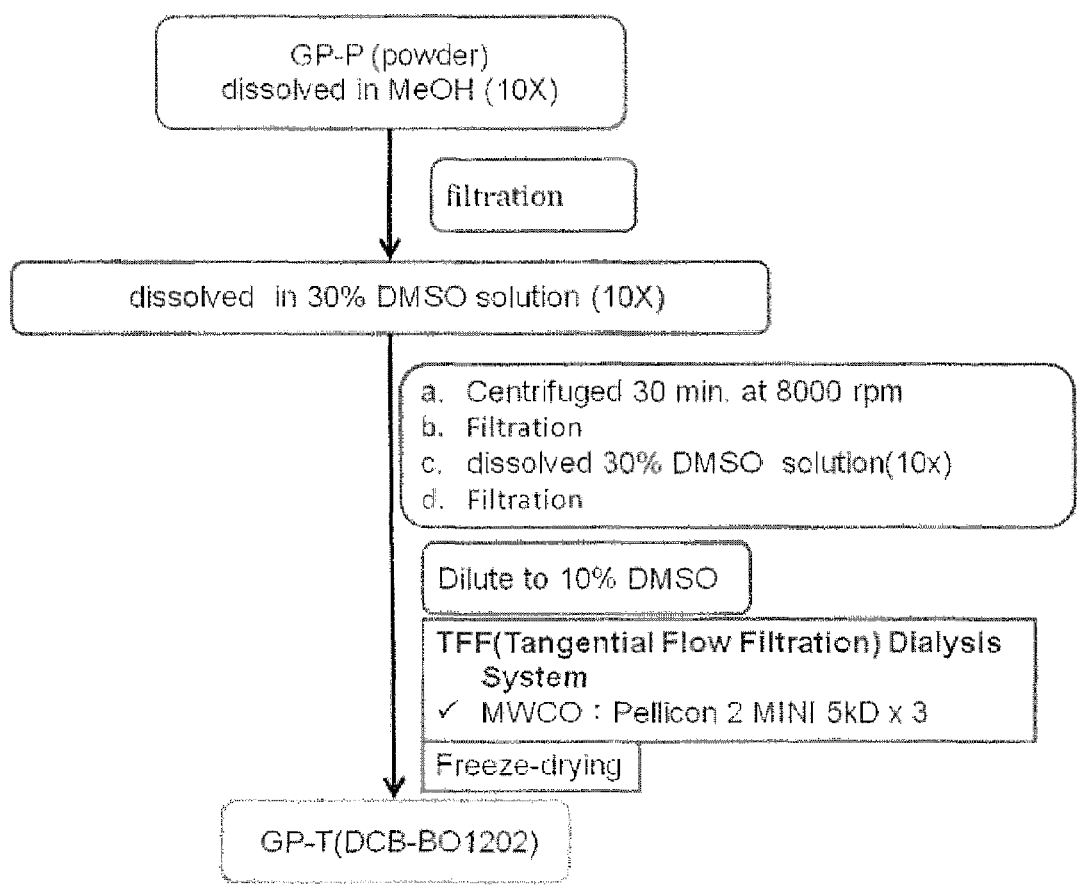
FIG. 1 shows a flowchart of a method for the preparation of GP active extracts in accordance with one embodiment of the invention.

Embodiments of the invention relate to methods for preparation of active fractions from a medicinal herb, such as powders of *Graptopetalum paraguayense* (fresh materials may be pulverized at lower temperatures (e.g., <40° C.) and concentrated to a small volume, followed by freeze drying). The starting materials (e.g., powders of *Graptopetalum paraguayense*) may be extracted with an alcohol (e.g., methanol) to remove methanol-soluble components. Then, the active fraction is extracted with 30% DMSO. After removal of precipitates by filtration, the filtrate is purified on a tangential flow filtration system using a suitable (e.g., 5 kD) molecular weight cutoff membrane and a specific solution containing 10% DMSO and double distilled water. This process affords the isolation of an active fraction, which is partially purified and concentrated. This process, after optimization of the parameters, is confirmed to be suitable for large scale production of the GP active ingredients. The conventional column chromatography methods cannot produce the active fractions GP-T of the present invention on the same scale. Furthermore, the conventional methods would take much longer and cost more, In accordance with embodiments of the invention, the starting materials of Graptopetalum paraguayense may use the parts that are above the ground, such as leaves. For example, GP-T active fractions described below may be obtained using the leaves of Graptopetalum paraguayense, which are subjected to the extraction and partial purification processes described herein. The Graptopetalum paraguayense powder starting materials may be prepared by grinding up the leaves, concentrating and freeze drying. The active fraction obtained is referred to as "GP-T" fraction, which is a partially purified active fraction.

The GP-T active fractions in accordance with embodiments of the invention have better activities than those of GP-P (see Example 3 below). After degradation experiments, the active components in the active fractions of the invention are found to contain various monosaccharides, in addition to phenol monomers, and the molecule weights of the active components are about 4-9 kD, which are different from the prior art GP-P extracts. Furthermore, the TFF system is more efficient than column chromatography (e.g., Sephadex LH-20). The TFF system can process 10 kg or more daily. It is more economical because it avoids the costs associated with the large amounts of solvents needed with column chromatography. This is the first time that TFF is used for the purification of GP extracts and the extracts thus obtained show higher activities. Thus, the methods disclosed in this application show unexpected results in both being economical and the products being more active.

Embodiments of the invention will be illustrated using the following specific examples. However, one skilled in the art would appreciate that these examples are for illustration only and other modifications or variations are possible without departing from the scope of the invention.

The following description encompasses four parts. The first part relates to the active fraction isolation and purification, which uses specific solvent to extract and isolate the active fractions. Then the extracts are purified and concentrated using ultra filtration with the use of a suitable cutoff membrane (e.g., 5 kDa cutoff). The parameters for large scale productions have also been confirmed.

The second part relates to in vitro tests. Hepatic stellate cell line (HSC-T6) from rats is a liver cancer cell line. Using this cell line, one can investigate the effects of the active fraction GP-T, which has been isolated from the GP-P extracts, on the regulation of TGF-β signaling and collagen formation, particularly with respect to the cumulative inhibition effects and the anticancer activities. Furthermore, the anti-fibrosis anti-cancer bioassays may be used to explore and confirm the active extracts preparation processes.

The third part relates to in vivo tests. Diethylnitrosamine (DEN) can induce liver fibrosis, liver cirrhosis, and liver cancers. Using these in vivo systems in rats, one may assay the activities of GP extracts, GP-P and GP-T, on the inhibition of liver fibrosis and liver cancer formation, and on the liver function protection. These tests may include analyses of serum chemistry, serum fibrosis factor, liver tumor nodule numbers, body weights, survival rates, and pathology sections.

The fourth part relates to active components analysis. These analyses may include the use of HPLC, such as using LiChrospher® Dial Column and commercially available monomeric and oligomeric procyanidins (DP2-DP10) as reference standards, to compare the active extract samples GP-T. The analysis may also include $^{13}$C-NMR and MALDI-TOF mass spectrometry analysis and comparison of the results with information in the literature. These assays indicate that the active components are tannins. These tannins may be further analyzed after phloroglucinol degradation. The degradation products may be analyzed for their components. GP-T may also be hydrolyzed with TFA to analyze their sugar components using high performance anion exchange column (HPAEC), to confirm the compositions of their active components.

Embodiments of the invention will be further illustrated with specific examples. One skilled in the art would appreciate that these examples are for illustration only and various modifications and variations are possible without departing from the scope of the invention.

Methods of Preparation

1. Extraction of Graptopetalum paraguayense Powders (GP-P)

GP-P is product obtained from Chuang Song Zong Pharmaceutical Co., Ltd. (Taiwan). GP-P is processed from a freeze dried powder of Graptopetalum paraguayense obtained from Nugentek LifeScience (Taiwan) Co., Ltd.

Other reagents and solvents may be from any commercial sources. The following lists non-limiting examples of various reagents and their sources in parenthesis: methanol and ethyl acetate (Macron); anhydrous methanol (Alfa Aesa); (−)-epicatechin, $C_{15}H_{14}O_6$, (Sigma); gallic acid, $C_7H_6O_5$, (Fluka); phloroglucinol ($C_6H_6O_3$), L-ascorbic acid, ($C_6H_8O_6$), and sodium acetate trihydrate ($CH_3COONa.3H_2O$) (Sigma-Aldrich); sodium sulfate and acetic acid (Merck).

Methods of Extraction

FIG. 1 shows a flowchart illustrating one method according to embodiments of the invention for the purification of GP active fractions. As shown in FIG. 1, GP-P powder is soaked in methanol (10× the weight of the GP-P powder). The methanol soluble components are removed by filtration. Then, the residues are treated with 30% DMSO (10× the weight of the GP-P powder). After extraction, the solid and liquid parts may be separated by centrifugation (e.g., 30 min., 8,000 rpm). The DMSO extract was further filtered to obtain an extract. The residue was treated with 30% DMSO (10×) one more time. The DMSO extract was collected by filtration and combined with the first extract.

The combined DMSO extracts were diluted with double distilled water to 10% DMSO concentration before subjecting the final solution to tangential flow filtration (dialysis). In this particular example, the TFF dialysis was performed with a Pellicon 2 MINI filter cartridge (5 kD cutoff; from. Millipore). The dialysis may be performed with more than once, by adding more solvent into the cartridge. Once the dialysis is complete, the retained fraction may be collected and dried (e.g., by freeze drying) to afford the purified active fractions of GP-T.

GP-T Analysis

The products may be analyzed using any suitable analytical instruments, such as HPLC. The following is an example, using an HPLC to analyze the above purified active fractions:

Instrument and Equipment
Column 1: LiChrospher® 100 Diol, 5 μm, 4.6×250 mm, Merck
Column 1: Develosil 100 Diol, 5 μm, 4.6×250 mm, Phenomenex
Sample preparation: GP-T (diluted with AWA)
AWA acetone/Water/acetic acid=70/29.5/0.5
Detection: UV 280 nm
Mobile phase A: $CH_3CN/HOAc=99/1$
Mobile phase B: $CH_3OH/H_2O/HOAc=94/5/1$
Elution mobile phase Profile:

| Time | A % | B % |
| --- | --- | --- |
| 0 | 97 | 3 |
| 25 | 75 | 25 |
| 45 | 40 | 60 |
| 55 | 10 | 90 |
| 58 | 10 | 90 |
| 60 | 97 | 3 |
| 70 | 97 | 3 |

Reference standards: Procyanidins (DP2-DP10) from Sigma.

| Compound | MW |
| --- | --- |
| Epi-catechin | 290.26 |
| EGCG | 458.3 |
| DP-2 | 588 |
| DP-3 | 876 |
| DP-4 | 1164 |
| DP-5 | 1452 |
| DP-6 | 1740 |
| DP-7 | 2028 |
| DP-8 | 2316 |
| DP-9 | 2604 |
| DP-10 | 2890 |

Figure 2:
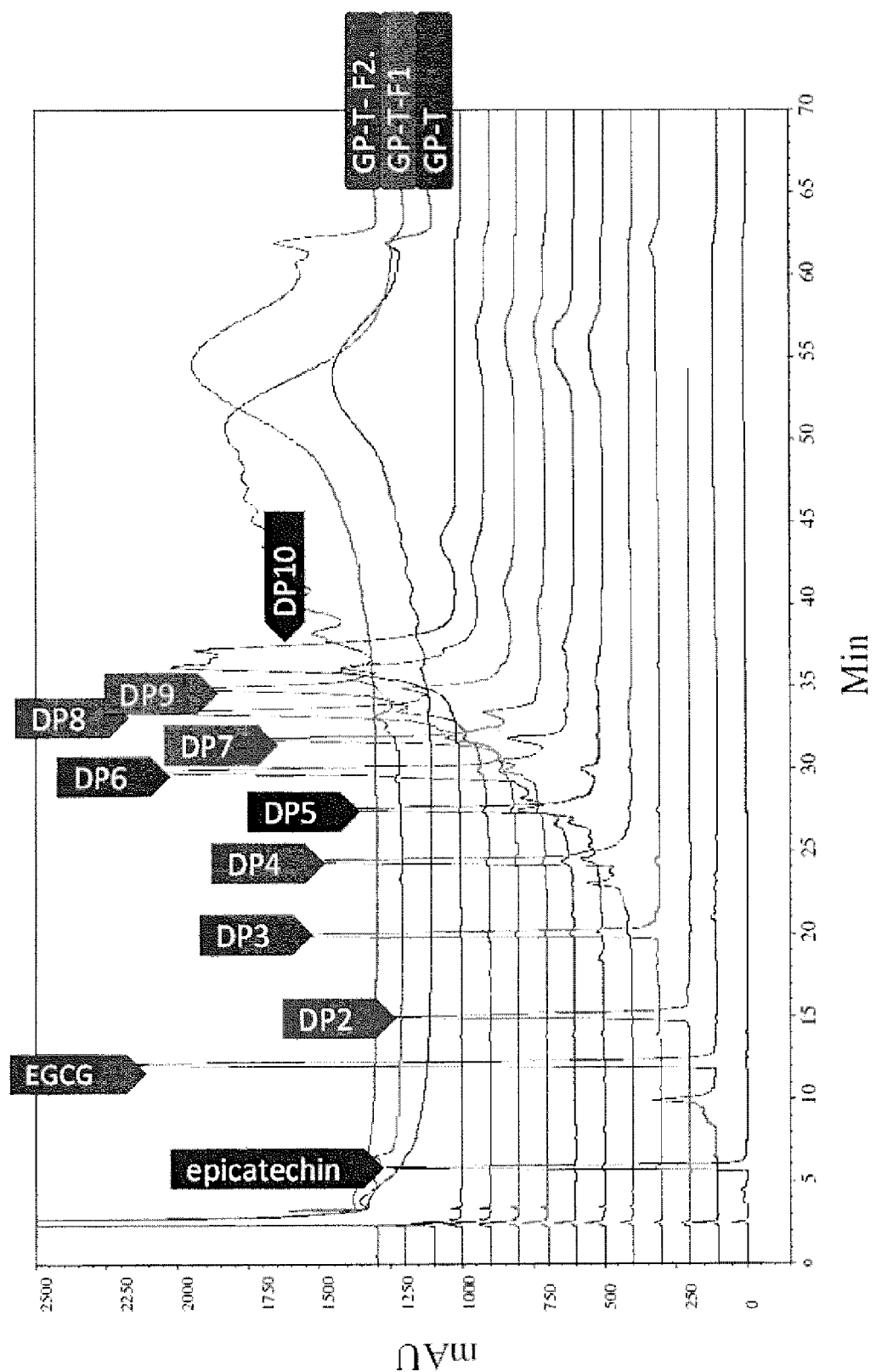
FIG. 2 shows HPLC profiles of GP-T extracts, compared to standards.

FIG. 2 shows HPLC profiles of the GP-T samples with the standards (DP2-DP10). In this analysis, the GP-T-1 sample is the ethanol insoluble fraction and the GP-T-2 sample is the ethanol soluble fraction when GP-T active extract is treated with ethanol. The ethanol insoluble fraction (GP-T-1) accounts for about 90% of the total, while the ethanol soluble fraction (GP-T-2) accounts for about 10%. Thus, the GP-T active fraction in accordance with embodiments of the invention contains substantially ethanol insoluble components. As used herein, the term "substantially insoluble" refers to less than about 20% of GP-T is soluble in ethanol, preferably less than about 15% soluble, and more preferably less than about 10% soluble. The HPLC shows that components in the GP-T active fraction have molecular weights higher than procyanidin DP-10 (MW=2,890). The components in the GP-T-1 fraction have larger molecular weights than those in the GP-T-2 fraction.

Figure 3:
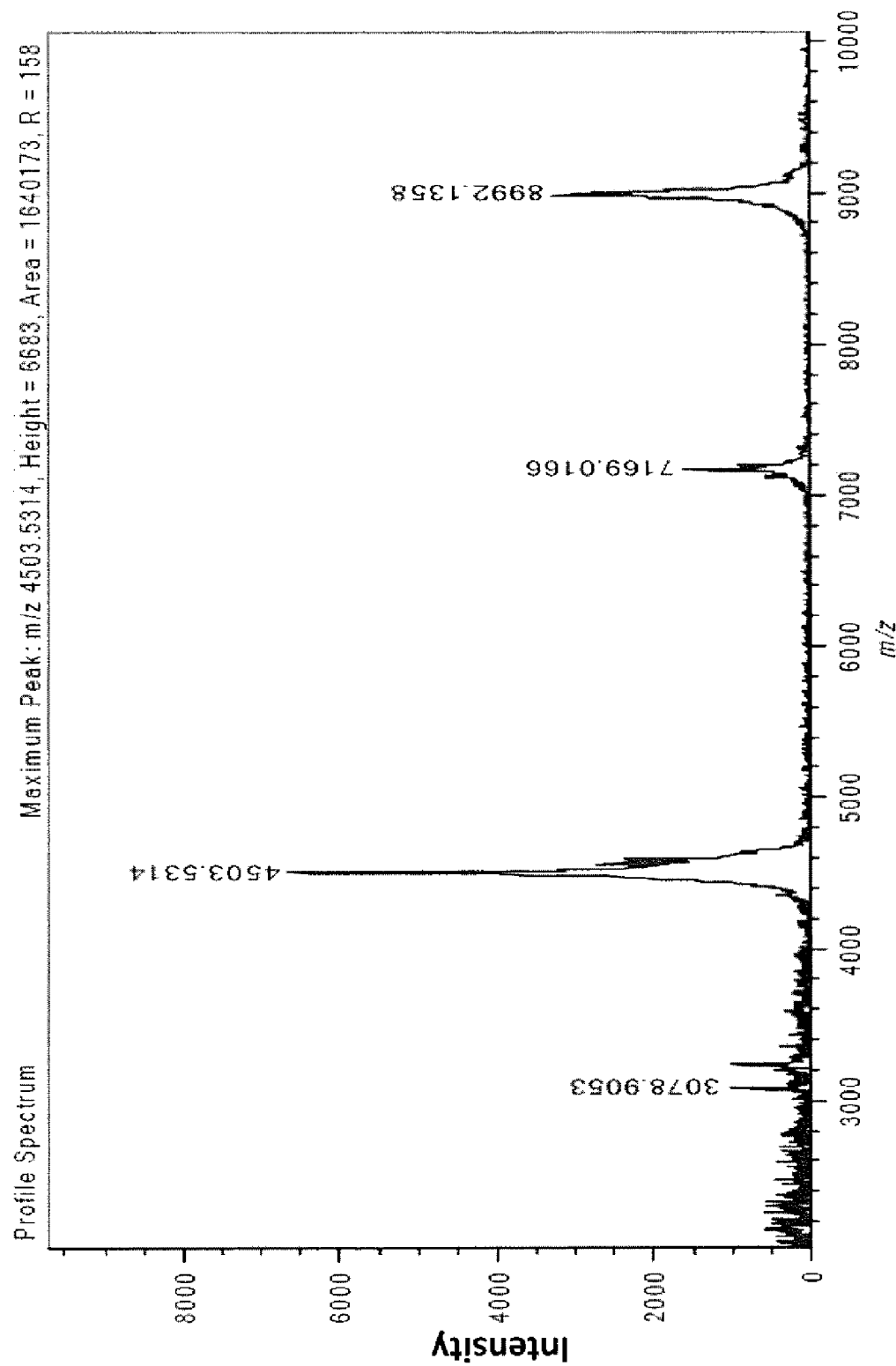
FIG. 3 shows a MALDI-TOF mass spectrum of a GP-T active fraction in accordance with one embodiment of the invention.

MALDI-TOF mass analysis confirms that these components have molecular weights larger than that of DP-10. The major peaks in MALDI-TOF comprise mainly peaks around 4.5 kD, 7.1 kD, and 8.9 kD, as shown in FIG. 3.

Figure 4:
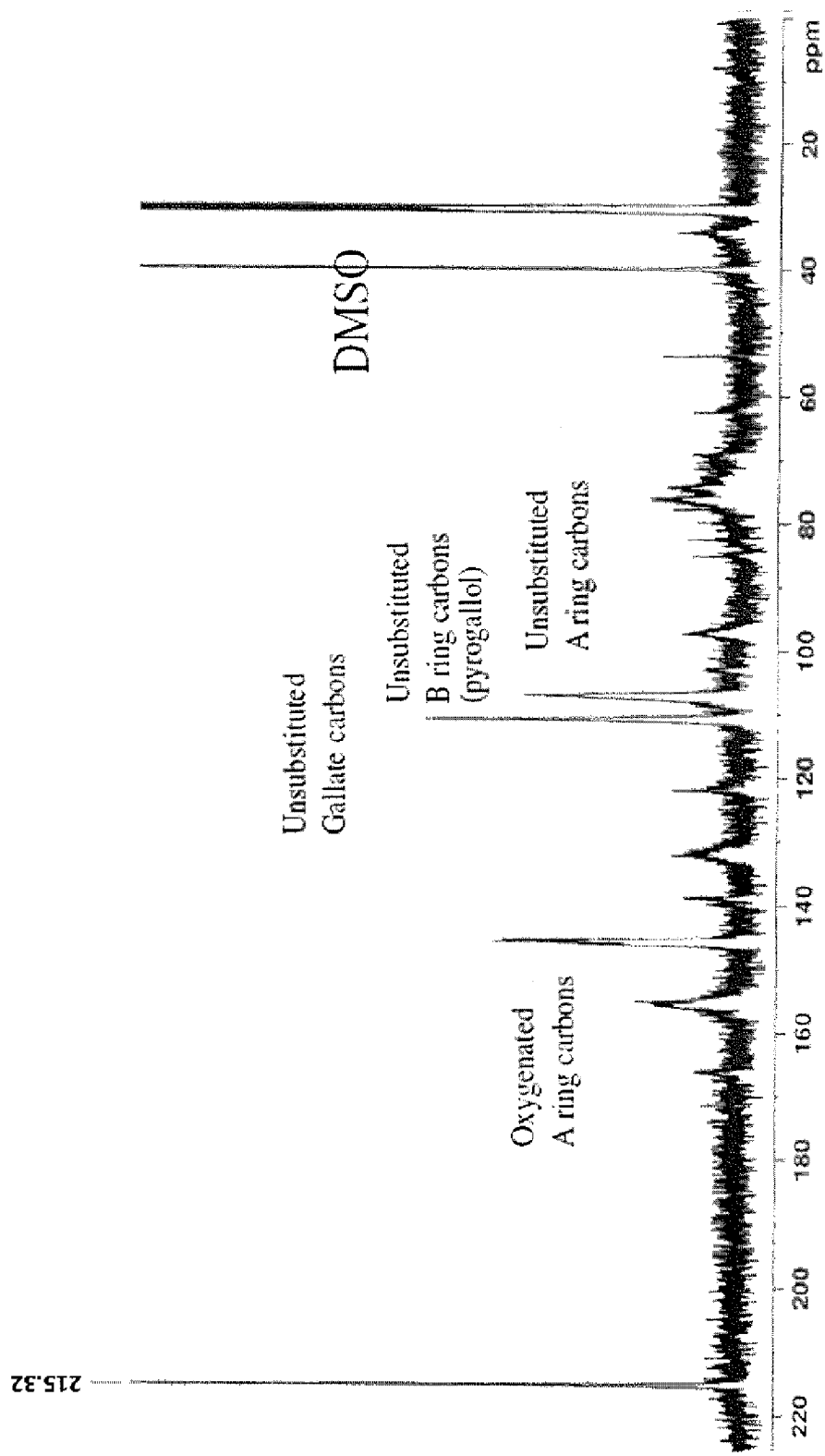
FIG. 4 shows a $^{13}$C-NMR spectrum of a GP-T active fraction in accordance with one embodiment of the invention.

FIG. 4 shows the $^{13}C$-NMR (in $D_2O$ acetone-$d_6$) spectrum of a GP-T sample. The spectrum indicates that the active fraction comprise mostly tannins, as compared with reference spectra in Phytochemical, 67, 2380-2391 (2006).

3. Pharmacological Studies

In Vitro Anti-Fibrosis and Anti-Cancer Tests

The active fractions of GP extracts were tested for their pharmacological properties using in vitro systems. Hepatic stellate cells (HSC, or astrocytes) and hepatoma carcinoma cell (HCC) lines are cultured in vitro. These cells are used to assess the activities of various batches candidate GP extracts for their anti-fibrosis and anti-cancer activities. Various hepatoma carcinoma cell lines were used to test the in vitro cytotoxicities of GP extracts: GP-P and GP-T. The tests were performed at five different concentrations for each. GP-P can inhibit hepatoma carcinoma cell lines, e.g., Huh7, HepG2, etc. Cell viabilities can be observed with the MTT cell viability assays. The 1050 values for these cell lines are all <50 μg/mL In addition, GP-P and GP-T can inhibit the growth of activated hepatic astrocytes, HSC-T6.

Animal Tests

In addition to the in vitro tests, the GP active fractions are also assesses using in vivo tests. The animal tests were performed using a diethylnitrosamine (DEN)-induced liver fibrosis and liver cancer model in Wistar rats. The GP extracts were tested in vivo for their abilities to inhibit liver fibrosis and liver cancer.

Briefly, Wistar rats were fed 0.01% DEN drinking water for 9 weeks to induce liver fibrosis, liver cirrhosis, and liver cancers. Four weeks after the DEN treatment, the rats were given orally different doses of GP-P and GP-T extracts. Blood serum samples were obtained prior to drug treatments and every two weeks after the drug treatments. The serum samples were subjected to blood chemistry analysis to assess the serum fibrosis factor concentrations. After six weeks of drug treatments, the rats were sacrificed and analyzed for the following biological markers.

Blood chemistry analysis: AST/ALT/r-GT/Bilirubin/Albumin/Cholesterol;

Plasma fibrosis factor analysis: hyaluronic acid/P3NP/laminin;

Live tumor nodule numbers, cancer incidence rates, and survival rates; and

Pathological section and assessments.

Specifically, five-to-six weeks old Wistar rats were obtained from the animal center at the National Taiwan University Medical School. The rats were given 100 ppm DEN drinking water, and they were weighed weekly at feeding times. Based on the increases in body weights, the concentrations of DEN were accordingly increased. The feeding of DEN was continued for 9 weeks, which is sufficient to induce the occurrence of liver cirrhosis and liver cancer. Liver cancers were removed from the rats for cancer recurrence study.

The test samples (GP-T) were tested at two different concentrations and administered to the rats for four weeks (from the ninth to the thirteenth week). Pirfenidone was used as a positive control. In the tests, each group included 6-8 rats. The tests were conducted using the rat model and different concentrations of the GP test samples in the food to assess their effects on liver fibrosis and liver cancer recurrence.

The above describes various aspects of embodiments of the invention. The following will use specific examples to further illustrate embodiments of the invention. Example 1 shows a specific example for the purification of GP-T active fractions. Example 2 shows composition analysis of the active fractions of GP extracts. Example 3 shows Assays for anti-fibrosis and anti-cancer activities of GP-T. Example 4 shows anti-fibrosis and anti-cancer activities in animal models. Example 5 shows pharmaceutical evaluation using an animal, in which DEN-induced tumor has been removed. These specific examples are for illustration only. One skilled in the art would appreciate that other modifications and variations from these specific examples are possible without departing from the scope of the invention.

Example 1

Preparation of GP-T

Methanol extraction: weigh 450 g of the starting material and put in a 5 L serum flask, and then add 4,500 mL methanol. The extraction was allowed to proceed for two days;

Remove the methanol extract by suction filtration, and put the residue in the serum flaks. 4,500 mL of 30% DMSO was added and the extraction was allowed to proceed for 5 days;

The 30% DMSO extract was collected by centrifuge at 4° C., 8,000 rpm for 30 min. The extract was stored at 4° C.;

Measure 4,000 mL of 30% DMSO extract and put in a 20 L empty bucket. Add 8,000 mL milli-Q water and mix well to produce 10% DMSO extract solution, which was allowed to stand for 2 days at 4° C.;

The extract solution was filtered through a filter with 1 μm pore sizes;

Then, the filtrate is further filtered through a second filter with 0.2 μm pore sizes;

Using a tangential flow filtration (TFF) system and a 5 ld) cutoff filter cassette, the above filtrate was circulated with a pump. The flow rate was adjusted and the feed end pressure is at about 12.5 psi, while the filtrate end pressure is at about 10 psi. Under these conditions, the filtrate comes out a t a rate of about 90-100 mL/min;

When the sample was concentrated to about 500 mL (about 1/20 of the original sample volume), the following solvents are continuously added using a peristaltic pump (with a flow rate at about 10-15): 10% DMSO (2.5 L, about ¼ of the original sample volume) and Milli-Q water (5 L, about 10 times the concentrated sample volume). The dialysis was continued until the volume became about 1/20 of the original sample volume;

Finally, the product was collected in a beaker from the retentate end. The product was lyophilized to afford a freeze-dried GP-T sample.

While the above procedure reports specific parameters for the preparation of GP-T, the specific parameters are provided for optimized production. One skilled in the art would appreciate that some or all of these parameters may be varied or modified without departing from the scope of the invention.

Example 2

Composition Analysis

Phloroglucinol degradation may be used to analyze the components that make up the active fractions of the GP-T samples. Briefly, a GP-T sample is hydrolyzed in the presence of acid and phloroglyucinol and the degradation products are then analyzed by a suitable analytic instrument, such as LC/MS. The following outlines a procedure for the degradation of a GP-T sample:

To a sample of GP-T (30 mg) was added 6 mL of 0.1% HCl in MeOH containing 50 mg/mL of phloroglucinol;

To the above solution was added 10 mg/mL of ascorbic acid;

The resultant solution was heated at 50° C. for 30 min.

To the reaction solution was added 30 mL of 40 mM $CH_3COONa$;

After evaporation of MeOH, the remaining aqueous mixture was partitioned with ethyl acetate (EA; at a ratio of 1:1); and The EA layer was analyzed with LC-MS.

For analysis using an LC/MS system, the following exemplary parameters may be used:

Column: Waters Associate; Symmetry Shield RP18, 5 μm, 4.6 mm×150 mm;

Detector: UV 280 nm and ESI-MS (Negative and Positive ions);

Injection volume: 10 μL

Sample: in MeOH

Flow rate: 1 mL/min

The mobile phase gradient is as follows:

| Time (min) | 1% acetic acid (%) | $CH_3CN$ (%) |
|---|---|---|
| 0 | 100 | 0 |
| 30 | 50 | 50 |
| 40 | 0 | 100 |
| 50 | 0 | 100 |

Figure 5A:
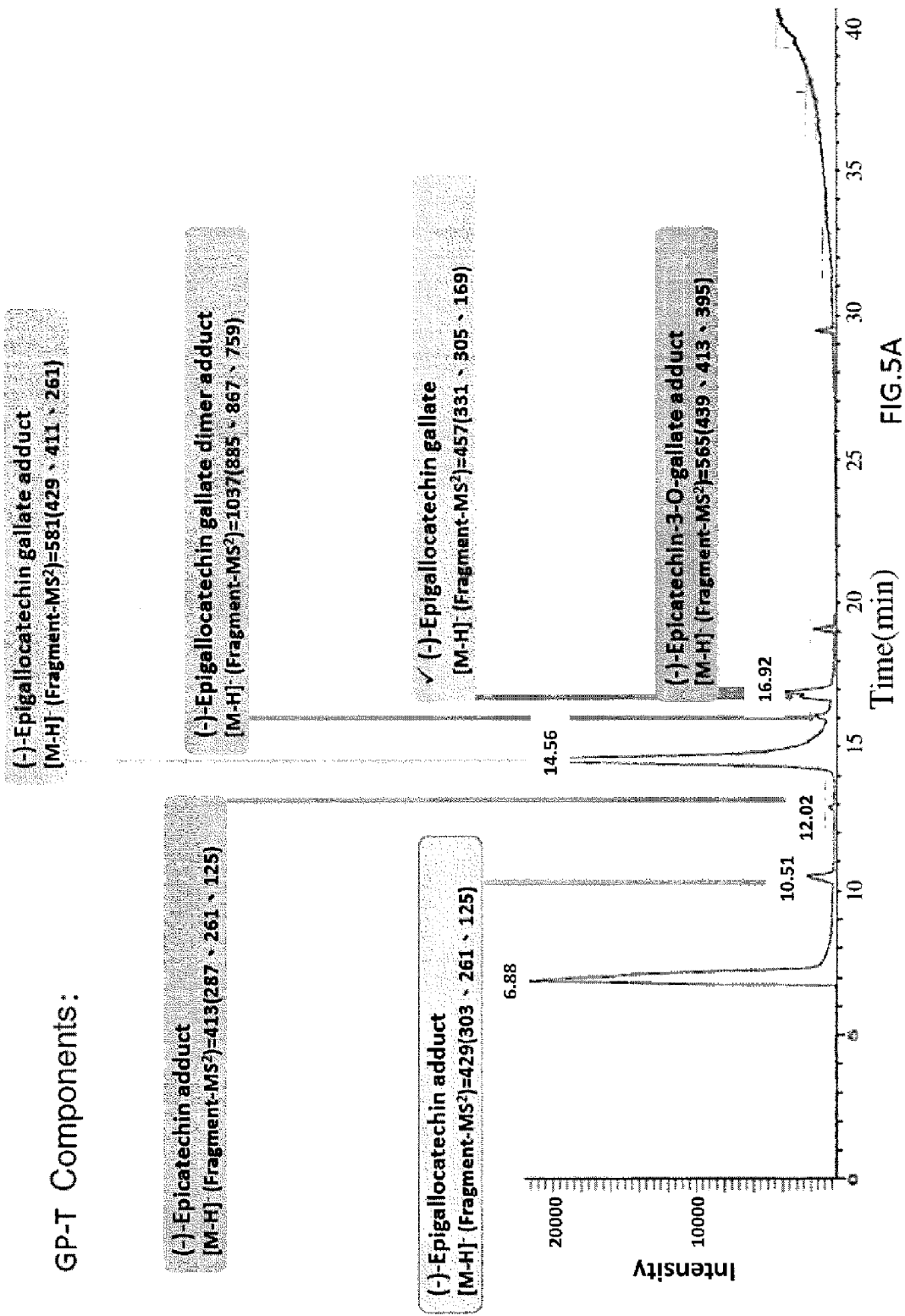
FIG. 5A shows LC/MS analysis of a GP-T active fraction in accordance with one embodiment of the invention.

FIG. 5A shows results from the LC/MS analysis. Based on this analysis, the active components in the GP-T active fractions are mainly large molecules of the polymeric tannins type. Based on phloroglucinol degradation reactions, it was found that active components mainly comprise (−)-epicatechin, (−)-epigallocatechin, (−)-epigallocatechin gallate, (−)-epicatechin-3-O-gallate, and (−)-epigallocatechin gallate as the building units. The active compounds are primarily compounds having (−)-epigallocatechin gallateas a terminal unit, or primarily compounds having (−)-epigallocatechin gallate as the major units.

To further identify the chemical entities in the GP-T samples the sample was subjected to LC/MS/MS analysis. The conditions for the LC column are:

UHPLC: dionex Ultimate 3000

Column: Thermo Hypersil Gold C18, 50×2.1 mm, 1.9 μm;

Sample: dissolved in 0.1% TFA;

Injection volume: 5 μl;

Gradient Conditions:

| Time (mins) | 0.1% FA in $H_2O$ | 0.1% FA in ACN | Flow Rate |
|---|---|---|---|
| 0 | 98% | 2% | 250 μL/mins |
| 0.5 | 98% | 2% | 250 μL/mins |
| 16 | 60% | 40% | 250 μL/mins |
| 19 | 5% | 95% | 250 μL/mins |
| 22 | 5% | 95% | 250 μL/mins |

MS analysis conditions:

Mass spectrometer: Thermo Scientific Q-Exactive

Electrospray Voltage: −3,500 V;

Normalized Collision Energy: 25 V;

Resolution: 140,000

Extraction Window: 5 ppm.

Figure 5B:
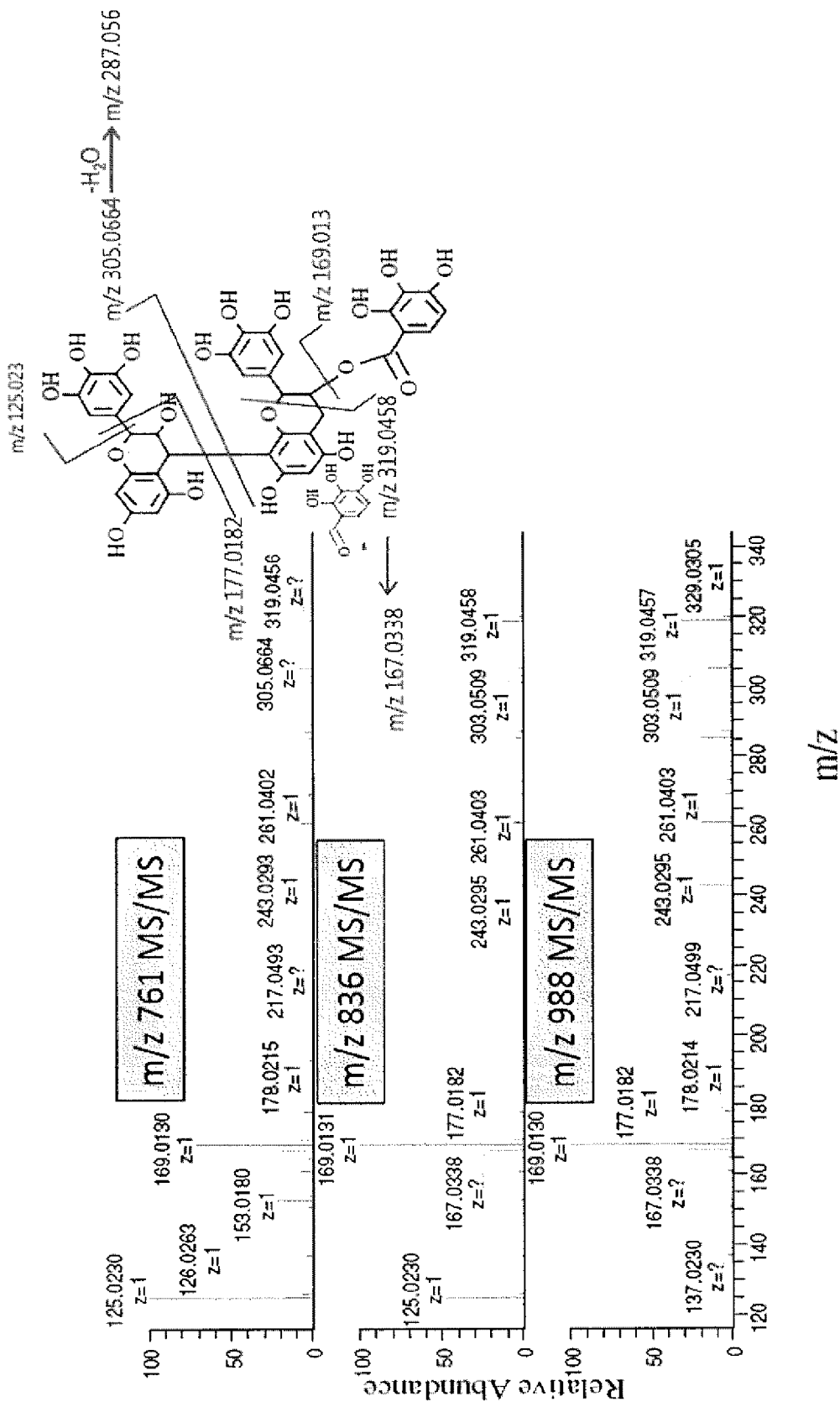
FIG. 5B shows MS/MS analysis of a GP-T active fraction in accordance with one embodiment of the invention.
Figure 5C:
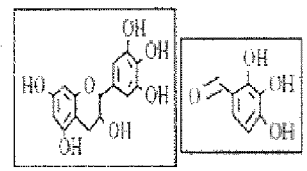
FIG. 5C shows summary of MS/MS analysis of GP-T active fractions.

FIG. 5B shows representative spectra from MS/MS analysis and a predicted structure of the tannin compound. FIG. 5C shows a summary table of a few representative peaks and their possible structures.

Sugar Composition Analysis

The GP-T active fraction was also subjected to sugar analysis. High-performance anion-exchange chromatography (HPAEC) can be used to analyze sugar compositions of polysaccharides based on anion exchange chromatography. This technique makes use of the negative charges on monosaccharide units to exchange with anions on the column. Different sugars can be eluted from such columns with mobile phases of different ionic strengths. The elution of different single sugar components can be monitored using an electrochemical detector with a pulsed amperometry gold electrode. The sample for analysis may be hydrolyzed using 1N trifluoroacetic acid (TFA) to produce monosaccharides, followed by lyophilization to remove TFA, for analysis using HPAEC.

The HPAEC mobile phase profile used in the analysis is shown in the following table.

| Time (min) | % A | % B |
|---|---|---|
| 0.1 | 100 | 0 |
| 25 | 100 | 0 |
| 30 | 0 | 100 |
| 50 | 0 | 100 |

Figure 6A:
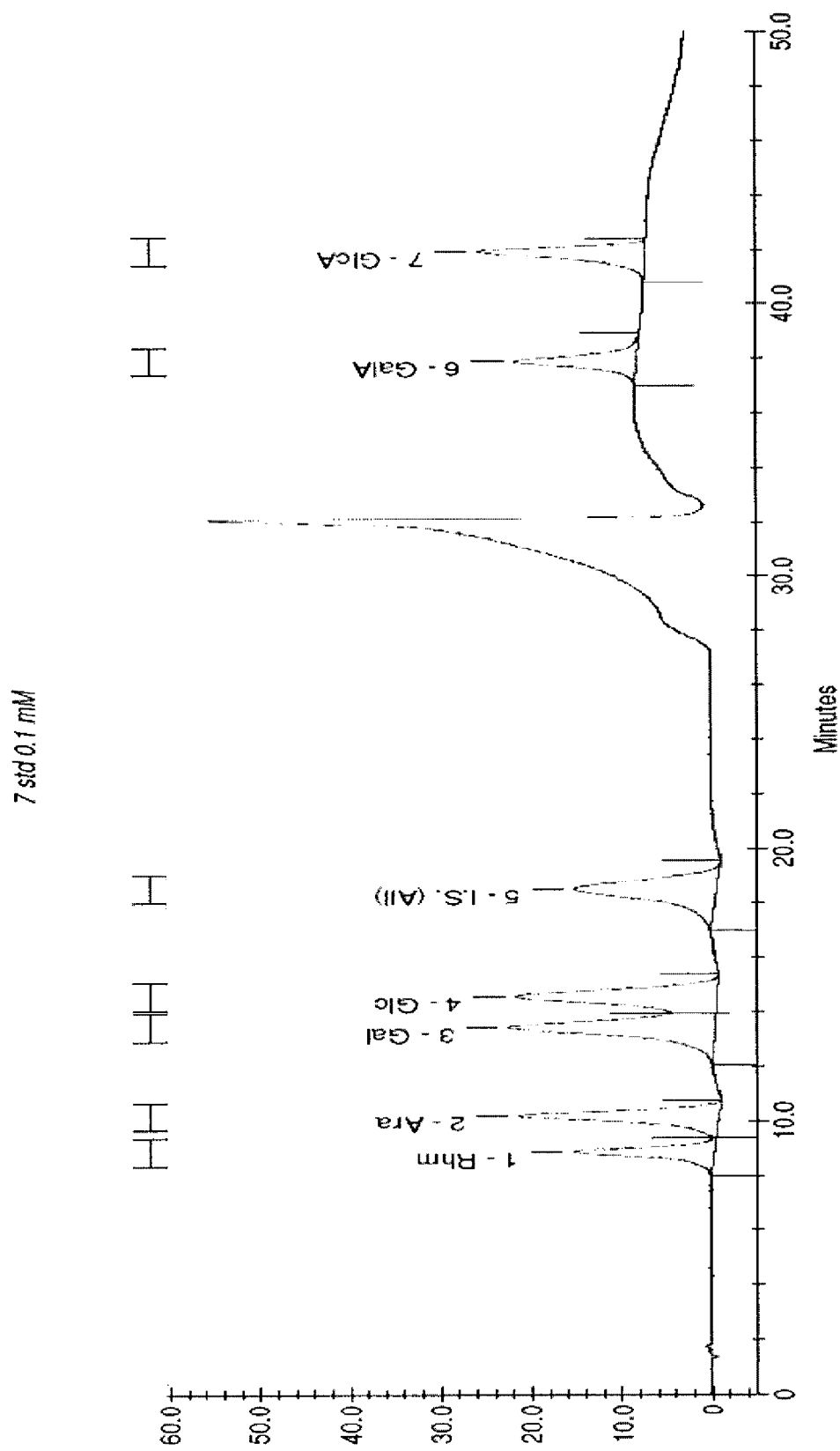
FIG. 6A shows a profile of standard carbohydrates in anion chromatography.

A: 8.75 mM $Ba(OH)_2$ solution which equilibrium to 17.5 mM NaOH
B: 100 mM NaOH, 100 mM NaOAc, 2 mM $Ba(OH)_2$ FIG. 6A shows various standard sugars in the HPAEC analysis. In FIG. 6A, the peaks labeled 1 through 7 are as follows: Rhamnose, Arabinose, Galactose, Glucose, internal standard, galacturonic acid, glucuronic acid, respectively.

Figure 6B:
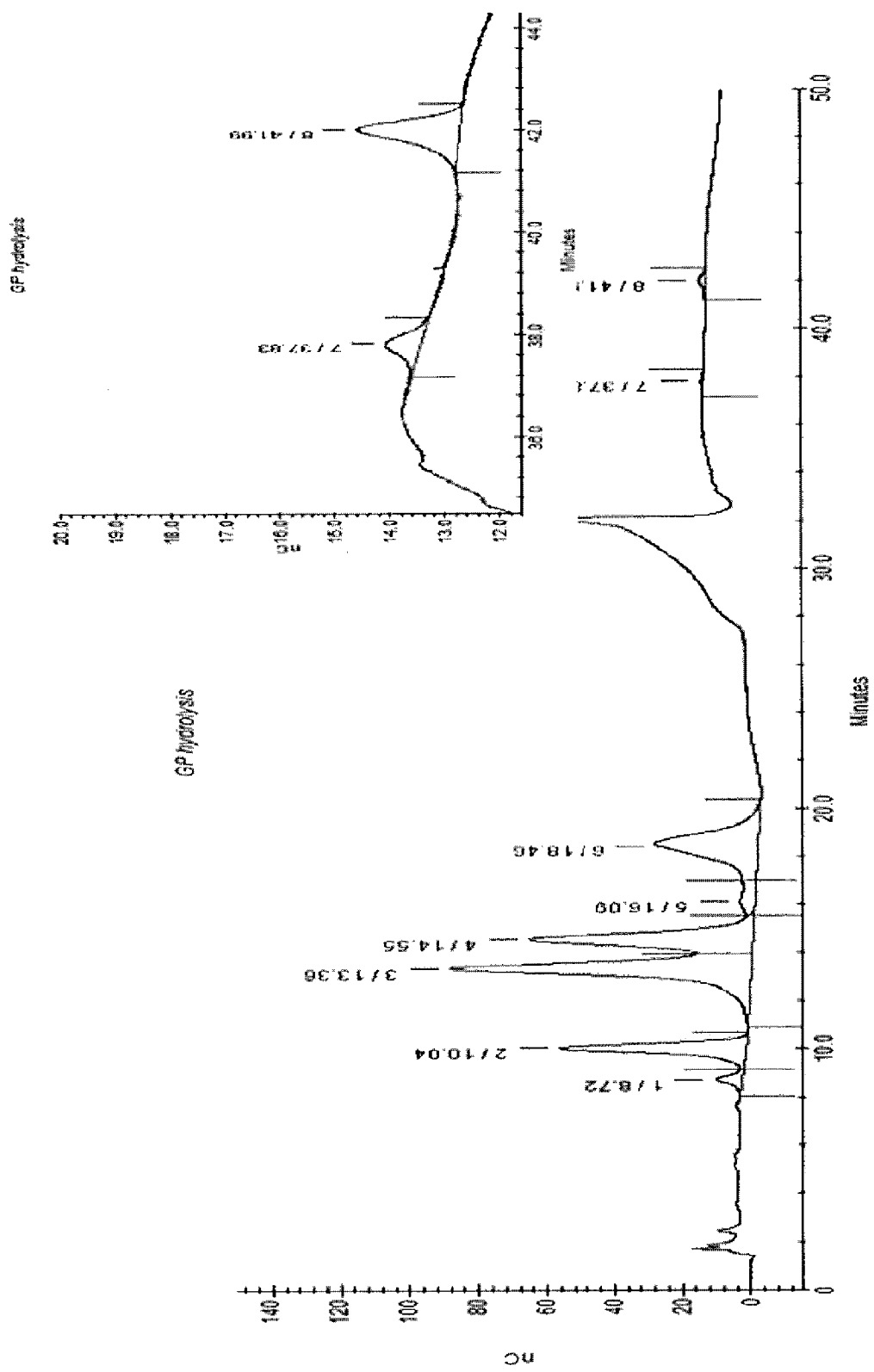
FIG. 6B shows a profile of carbohydrate analysis of GP-T in accordance with one embodiment of the invention.

FIG. 6B shows the HPAEC analysis results of TFA hydrolysate of a GP-T sample. From these results, it can be concluded that the GP-T active fraction contains arabinose, galactose, and glucose as the major sugars, and contains rhamnose, galacturonic acid and glucuronic acid as minor components.

Example 3

Assay for Anti-Fibrosis and Anti-Cancer Activities of GP-T

The biological activities of GP-T active fraction was analyzed using in vitro assays. Specifically, in vitro cell cultures of liver astrocytes and hepatocarcinoma cells (HCC) were used as for the analysis of the anti-fibrosis and anti-cancer activities of the GP candidate products. Using this bioassay system, the GP extract preparation procedures were investigated and the activities were confirmed.

First, using HCC cell lines, the GP-P extract (HH-F3) disclosed by Huang (U.S. patent application publication No. 2012/0259004) was compared with different batches of the GP-T extracts of the present application for their cytotoxicity and their abilities to inhibit oncoprotein expression (AURKA, CEP55) in the HCC cell lines.

Next, the bioassay platform was used to assess GP-T preparation processes and to assess their anti-fibrosis and anti-cancer activities. For example, the expression levels of AURKA/B (Aurona kinase A/B), CEP55 (55 kDa centrosomal protein), PTEN (phosphatase and tensin homolog protein), and α-SMA (alpha-smooth muscle actin) in HSC-T6 and HCC cell lines are used to compare the activities of equal doses of different batches of GP preparations: GP-Ta, and GP-Tb (from the GP-T preparation procedures), as well as products from different preparation procedures: GP-T, GP-C2 (including DMSO), versus GP-W2 (DMSO removed). The results show that the procedures GP-T, GP-W2 and GP-C2 produced extracts that have similar anti-fibrosis and anti-cancer activities as those of the HH-F3 extract disclosed in Huang (US 2012/0259004).

Next, one can assay the anti-fibrosis activities of different batches of GP-T extracts. Using rat liver astrocyte line, HSC-T6, one can study the effects of different batches of GP-T extracts on TGF-β signaling regulation mechanism and the inhibition of collagen formation accumulation. Two different batches of GP-T extracts, GP-8-4 and GP-8-4-2, at two different doses are were used to assess the effects on expression levels of COL I and III and smooth muscle α-actin in the HSC-T6 cells, in the presence or absence of TGF-β induction. The results from this study indicate that in the presence of TGF-13 induction, both extracts show an effective dose of about 50 ug/mL. Therefore, these two batches do not show significant difference in their anti-fibrosis activities.

Figure 7A:
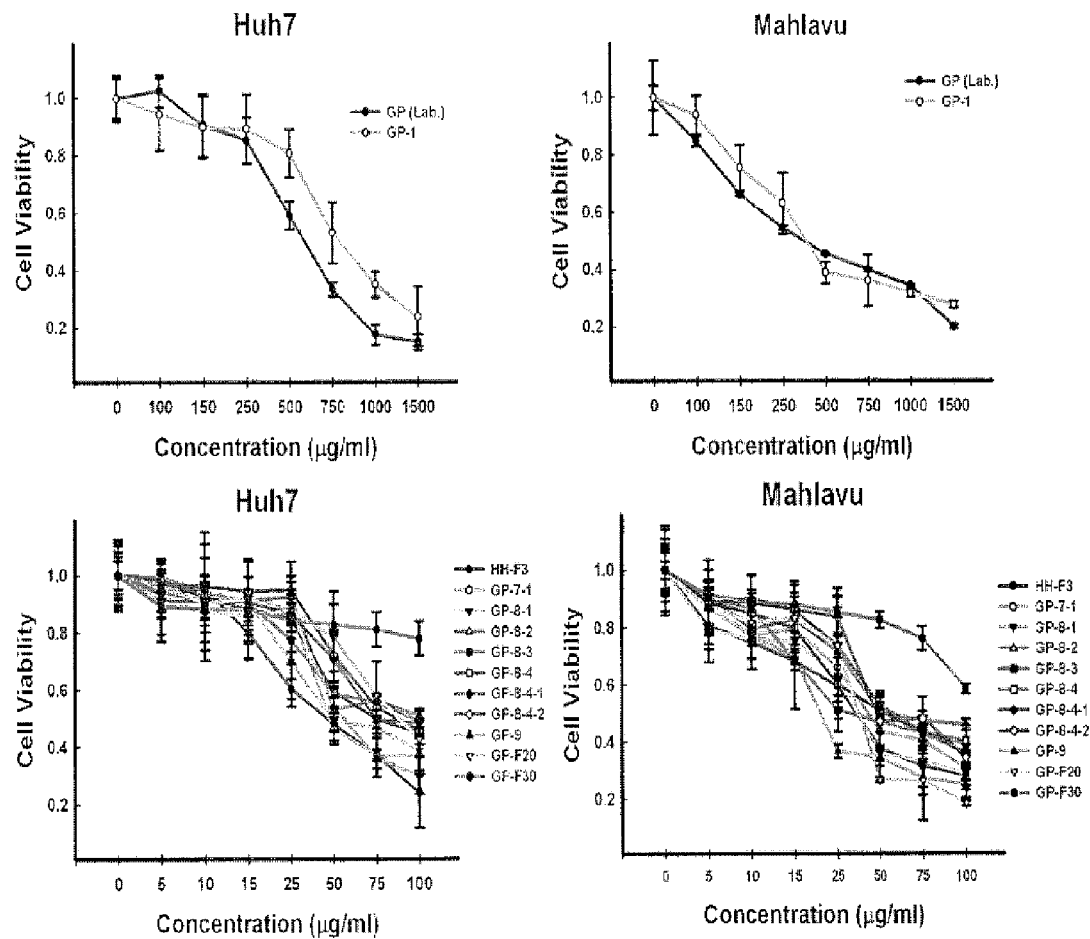
FIG. 7A shows inhibition of liver cancer cells by GP-T extracts in accordance with embodiments of the invention.
Figure 7B:
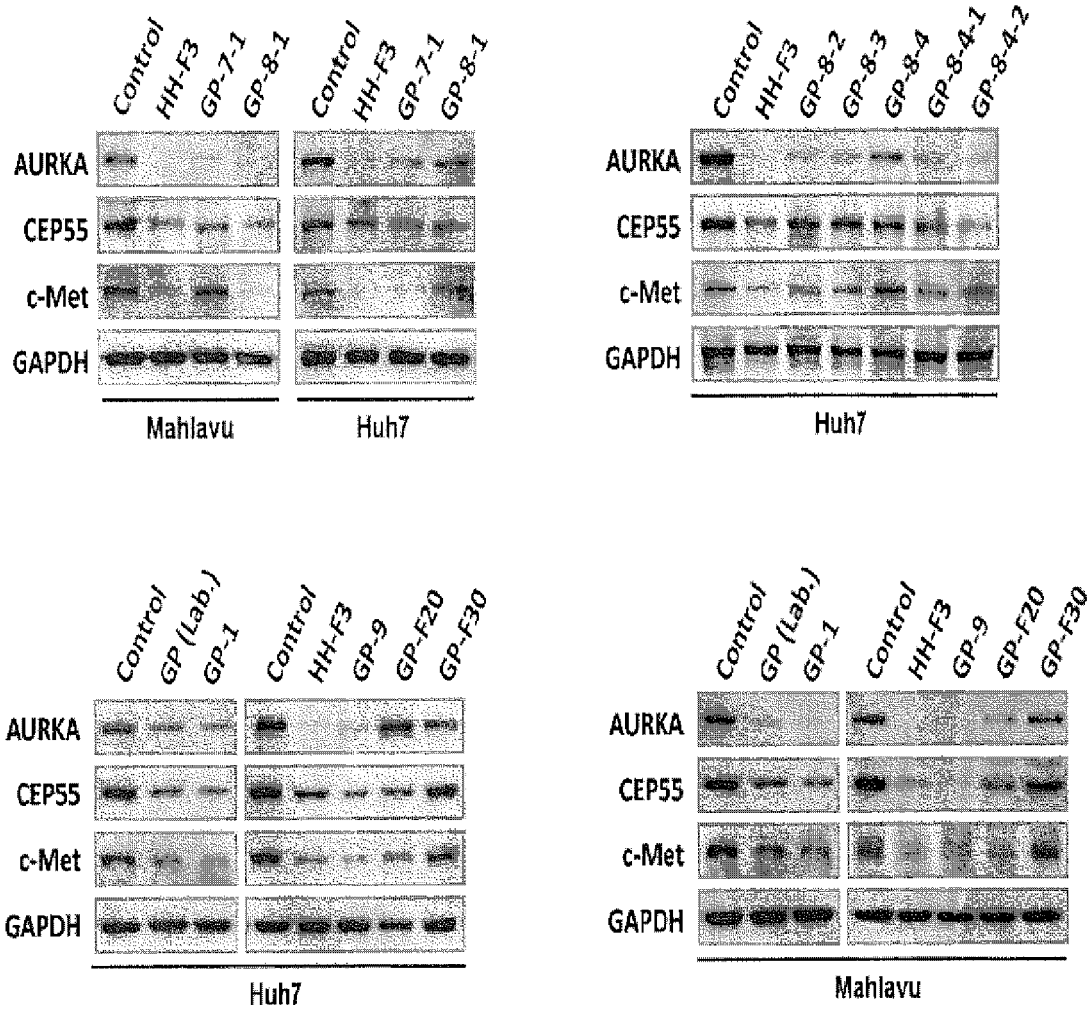
FIG. 7B shows inhibition of oncoproteins expression by GP-T extracts in accordance with embodiments of the invention.

FIG. 7A shows that various batches of GP-extracts have cytotoxicities against HCC cell lines. FIG. 7B shows effects of various GP extracts on oncoprotein expressions in HCC cell lines. The results show that the GP extracts have the abilities to inhibit oncoprotein expressions in the HCC cell lines (Huh7 and Mahlavu).

These test results are summarized in the Table shown in FIG. 7C. In this table, GP, GP-1, HH-F3, GP-7-1, GP-8-1, GP-8-2, GP-8-3, GP-8-4, GP-8-4-1, GP-8-4-2, GP-9, GP-F20, and GP-F30, respectively, represent GP-P (reference sample from Yang Ming Medical University, Taipei, Taiwan), GP-P (from Development Center for Biotechnology, Taipei, Taiwan), active fraction from Yang Ming Medical University, and the remaining are different batches of GP-T extracts.

The results shown in FIG. 7C indicate that GP-P and GP-T are both effective in killing (cytotoxic) HCC cell lines Huh7 and Mahlavu. The IC50 values differ by about 5 folds, with the GP-T extracts showing activities superior to that of GP-P. The overall effects of these active fractions can be summarized as: GP-9, HH-F3>GP-7-1, GP-8-1>GP-8-4-1, GP-8-4-2>GP-8-2, GP-8-3, GP-8-4>GP-F20>GP-F30.

Figure 8A:
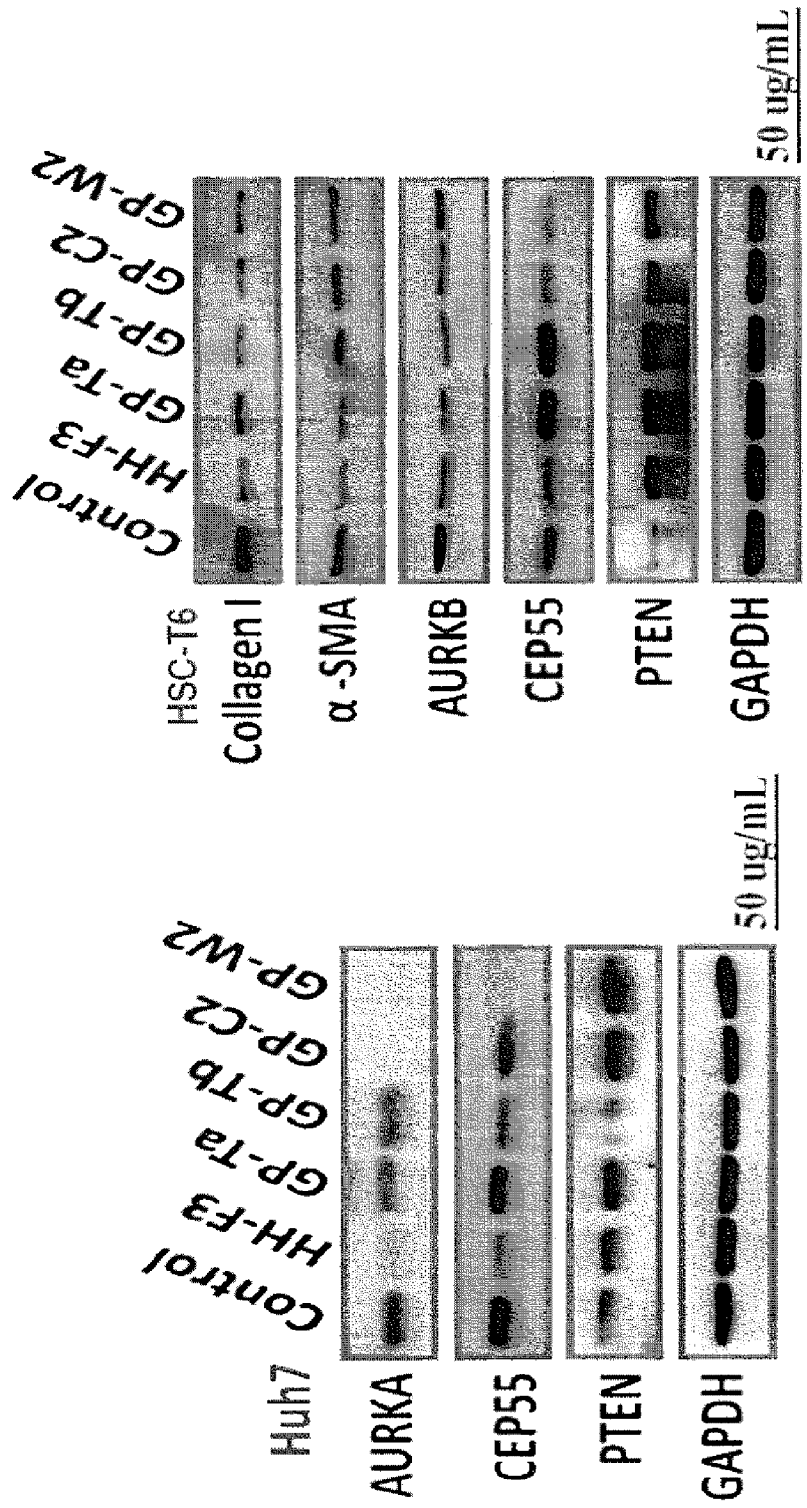
FIG. 8A shows results of using the bioassay system to investigate the GP-T preparation processes.

The bioassay system (antifibrosis and anticancer assays) may be used to monitor or modify the GP-T active fraction preparation processes. For example, FIG. 8A shows the use of oncoprotein expressions to monitor different batches of the GP-T extracts. The result shown in FIG. 8A indicate that the anti-fibrosis assay and anticancer assay can be used to confirm the optimal preparation processes for the preparation of GP-T active fractions. Under the confirmed preparation conditions, two different batches of GP-T extracts can have similar or identical activities.

Similarly, AURKA/B (Aurona kinase A/B), CEP55 (55 kDa centrosomal protein), PTEN (phosphatase and tensin homolog protein), and α-SMA (alpha-smooth muscle actin) protein expression in HSC-T6 and cancer cell line (Huh 7) may be used to monitor different batches of GP-T, GP-Ta, and GP-Tb from the same process, as well as extracts produced by different preparation processes: GP-T, GP-C2 (containing DMSO), and GP-W2 (with DMSO removed). The results shows that using the finalized preparation process, the GP-T active extracts (GP-W2 and GP-C2) have similar antifibrosis and anticancer activities as compared to HHF3 (see FIG. 8B).

Figure 8B:
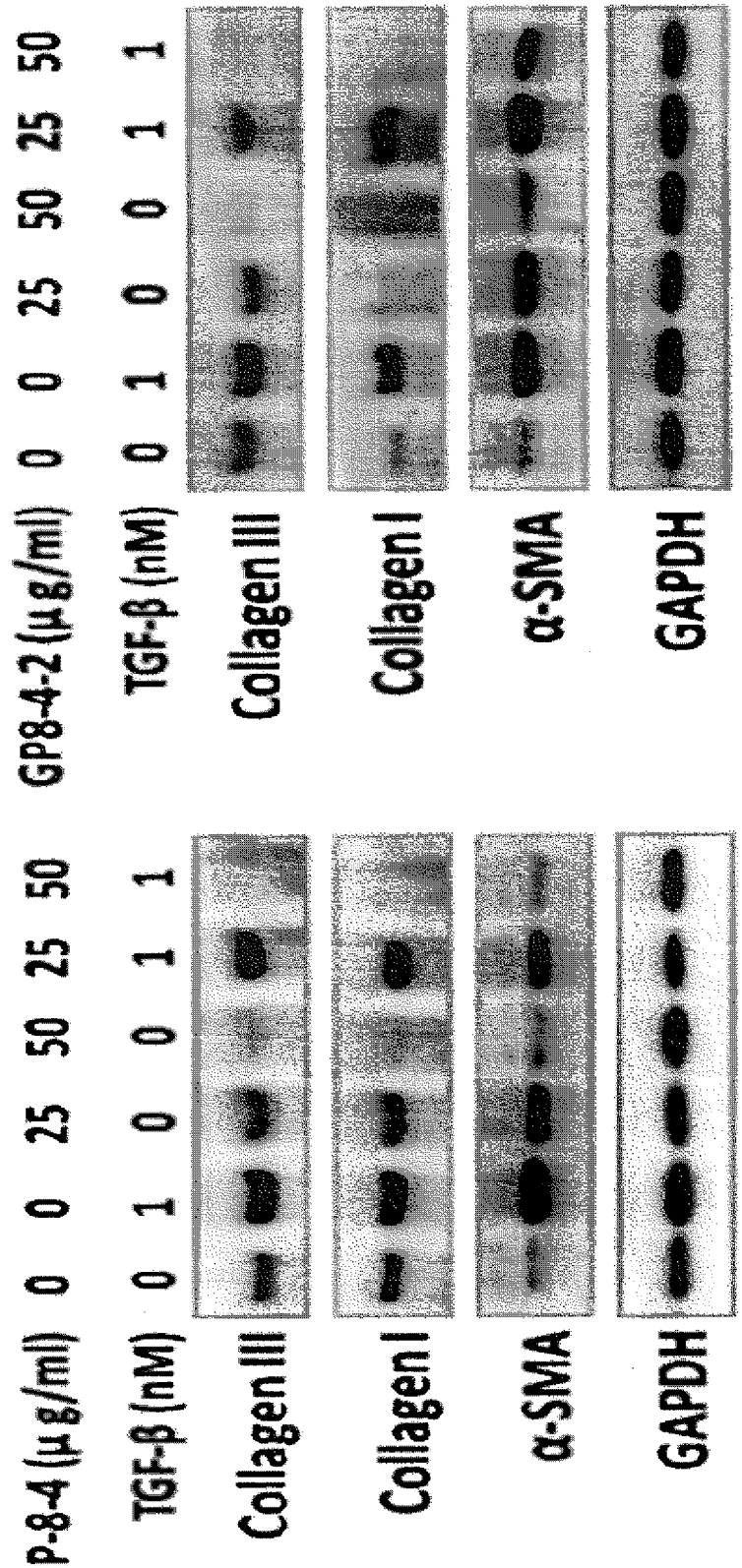
FIG. 8B shows the use of bioassays to confirm the preparation process in accordance with embodiments of the invention.

FIG. 8B also shows that in the presence and absence of TGF-β induction, one can analyze COL I and III and α-smooth muscle actins protein expression levels in HSC-T6. The results show that in the presence of TGF-β induction, both GP-8-4 and GP-8-4-2 have similar antifibrosis activities. The effective doses for both are about 50 μg/ml (FIG. 8B).

Example 4

Anti-Fibrosis and Anti-Cancer Activities in Animal Models

Experimental groups: animal groupings depend on experimental designs. Generally, the control group includes N=6-8 rats; the DEN group, drug group, and positive control groups (e.g., sarofenib (30 mg/kg), GP-T 50 mg/kg and 150 mg/kg) each include an average of 10-12 rats. The remaining rats may be used as the DEN induction group for the study of survival rates in DEN induction.

Statistical analysis: data are presented as mean±SEM. T-test is used to calculate the p values using the Prism statistics software, wherein $p<0.05$ indicates significant difference and is indicated by *; $p<0.01$ indicates highly significant in difference and is indicates by ; and $p≤0.001$ indicates extremely significant difference and is indicated by *. Alternatively, the statistical analysis may be performed using one way ANOVA and analyzed with Turtkey. If no identical symbols are indicated between different groups, it means that the difference between them is significant ($p<0.05$).

4-1: Application of GP Extracts Significantly Improves Body Weights, Liver Tumor Nodules, and Tumor Incidence Rates in the DEN Rats Whether GP-T extracts can inhibit DEN induced rate liver cancer can be assayed using body weight measurements and liver nodule sizes and numbers. Rats fed 50 mg/kg and 150 mg/kg GP-T extracts for six weeks were sacrificed and the livers were assessed for the nodule numbers and nodule lengths and widths, which were then used to calculate the nodule volume based on $V=L \times W^2/2$. Tumor nodules having any dimension larger than 3 mm were counted as a nodule. These parameters were used to assess the ability of the test drug to prevent DEN rat liver fibrosis, liver cirrhosis, and liver cancer incidence rates and cancer extents.

Based on body weight changes, nodule volumes, nodule numbers, cancer incidence rates, and results shown in the following Table:

| Group | Treatment Duration - 6 weeks | |
|---|---|---|
| | Weight Changes (g) | Survival Rate (%) |
| Normal | 48.0 | 100 |
| DEN | 032.9 | 73 |
| Sorafenib (30 mg/kg) | 19.5 | 100 |
| GP-T 50 mg/kg | 30.4 | 91.7 |
| GP-T 150 mg/kg | 55.5 | 100 |

Figure 9A:
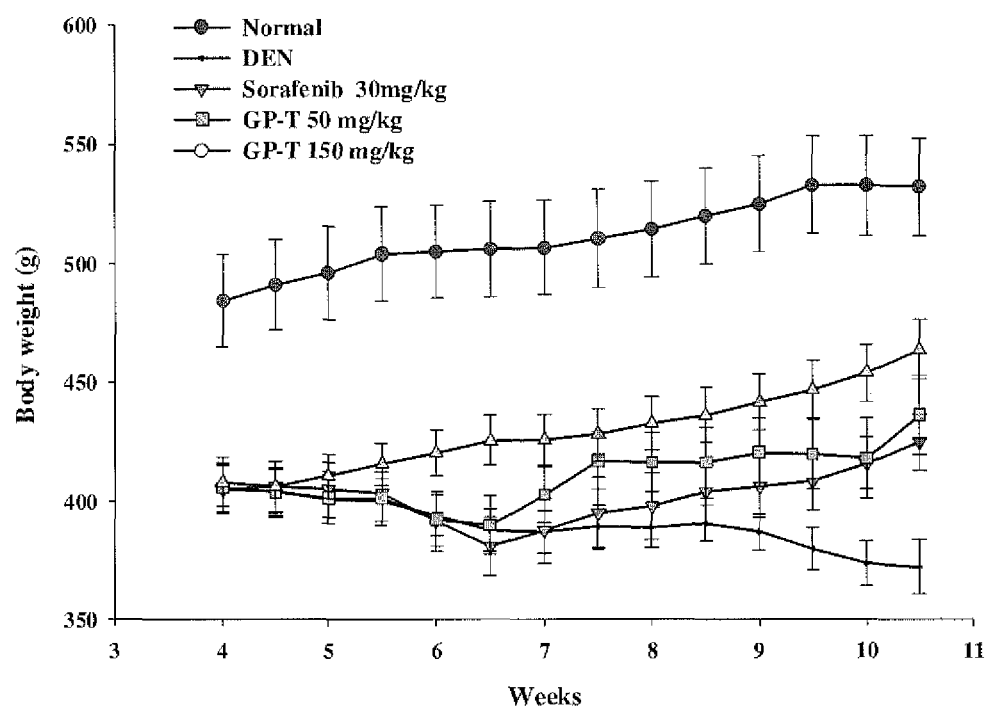
FIG. 9A shows body weight changes during treatments with GP-T in accordance with embodiments of the invention.
Figure 9B:
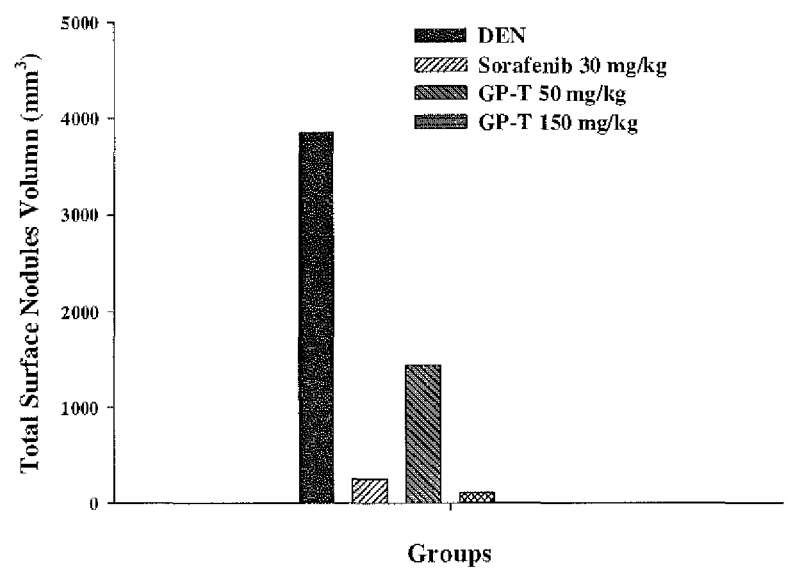
FIG. 9B shows results of inhibition of tumor formation by GP-T extracts in accordance with embodiments of the invention.

FIG. 9A shows the body weight changes during the treatment period. FIG. 9B shows the total surface nodule volumes for different treatment groups. These results are from experiments using body weights and liver tumor nodule volumes to assess whether GP-T can inhibit DEN-induced liver cancers in rats. The rats were fed orally 50 mg/kg or 150 mg/kg GP-T active extracts for six weeks. Then, the rats were sacrificed to measure the nodule numbers and the nodule lengths and widths. The volume of the nodules are calculated based on $V=L \times W^2/2$. The numbers of nodules are counted for any nodule larger than 3 mm in any dimension. These parameters are used to assess whether the GP-T extract can inhibit the rate and extent of DEN-induced liver cancer formation.

It is clear that GP extracts can reduce DEN-induced rat liver nodule volumes, nodule numbers, and maintain body weight gains. With respect to maintaining body weight gains, survival rates, and tumor incidence rates, the DEN-treated group had a survival rate of 73%, while the GP-T treatment groups had 100% survival. Therefore, GP shows excellent activities in the prevention of DEN-induced cancer death. With respect to maintaining body weight gains, the 150 mg/kg GP-T treatment group showed substantial body weight gains—during the same six-week treatment period, the normal rat grew 48 g on average; the DEN treated group lost 32.9 g; and the 30 mg/kg sorafenib treatment group gained 19.5 g (about 50% of the normal group). Thus, the GP-T treatment group had better effects in maintaining body weight gains, as compared to the sorafenib group. Particularly, the group treated with 150 mg/kg GP-T gained 10% more body weight, as compared to the normal group. In the 150 mg/kg GP-T treatment group, the tumor incidence rate (2 out of 12) and tumor total volume (42.4 mm$^3$) in the DEN treated rats indicate that liver cancer growth is significantly inhibited by the GP-T treatment.

Results from these experiments show that GP can significantly reduce liver damages and body weight loss that are induced by DEN treatment. The group treated with 150 mg/kg shows the best effects, even better than the positive control group treated with 30 mg/kg sorafenib.

4-2: GP Treatment Significantly Improves Serum Fibrosis Factors in DEN-Treated Rats ELISA can be used to analyze serum fibrosis factor contents, thereby to assess whether GP-T treatments can inhibit DEN-induced liver fibrosis in rats. The experimental design was to treat rats that had liver damages by oral administration of 50 and 150 mg/kg of GP-T extracts. The treatment was continued for six weeks. Serum samples were obtained prior to GP-T treatments and at the time the rats were sacrificed. The serum samples were analyzed for hyaluronic acid, Procollagen-3 N-Terminal Peptide (P3NP), and laminin contents in the sera.

Figure 10A:
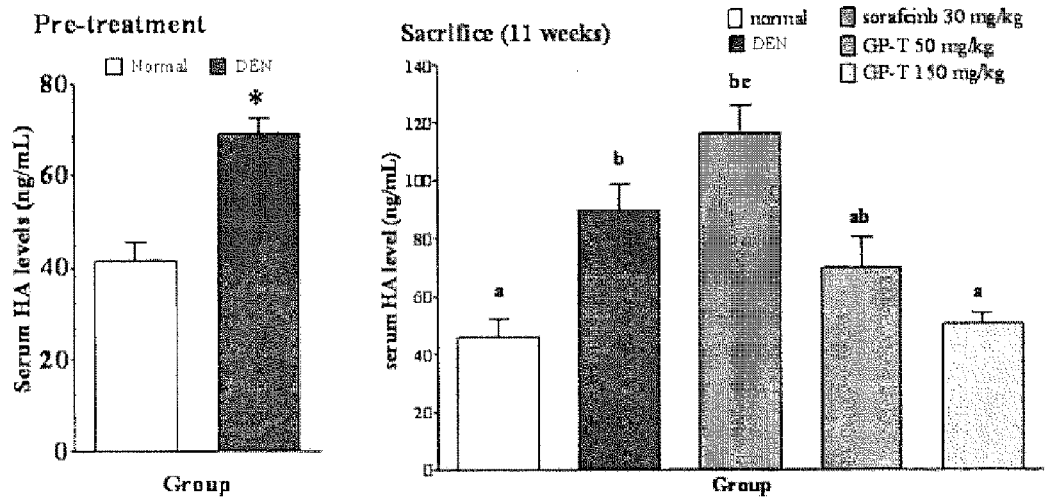
FIG. 10A shows serum hyaluronic acid levels of treatments with various agents in accordance with embodiments of the invention.
Figure 10B:
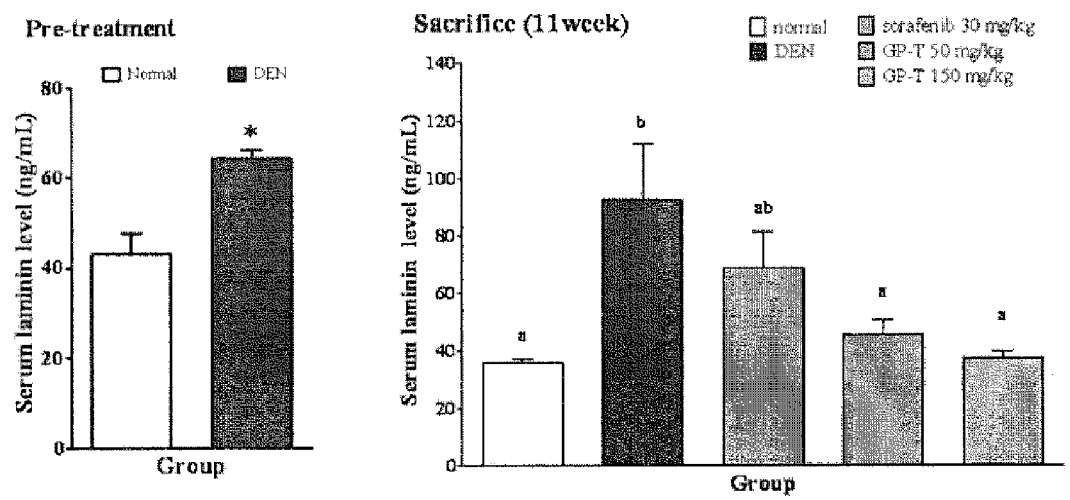
FIG. 10B shows serum laminin levels of treatments with various agents in accordance with embodiments of the invention.
Figure 10C:
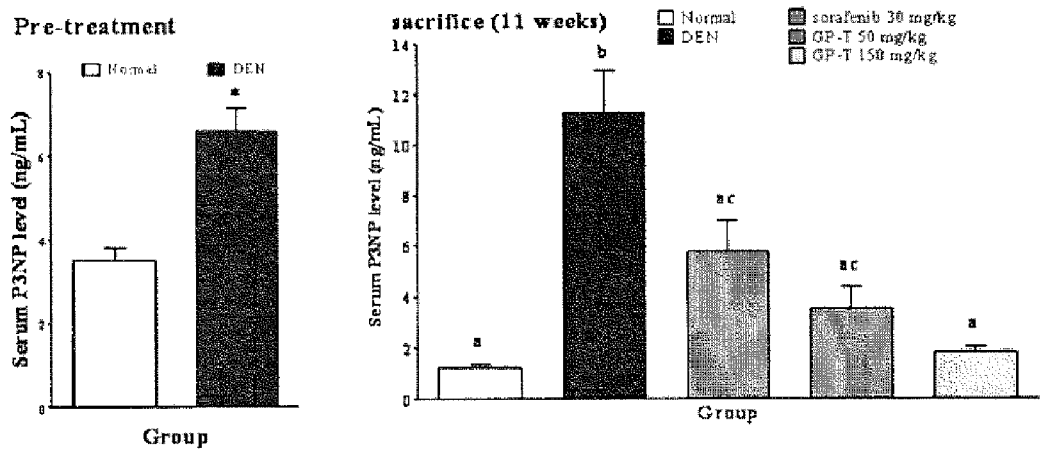
FIG. 10C shows serum procollagen-3 N-terminal peptide (P3NP) levels of treatments with various agents in accordance with embodiments of the invention.

FIG. 10A shows changes in the serum hyaluronic acid contents before and after treatments with various agents. FIG. 10B shows changes in serum laminin contents before and after treatments with various agents. FIG. 10C shows changes in serum Procollagen-3 N-Terminal Peptide (P3NP) contents before and after treatments with various agents.

These results show that 50 mg/kg GP-T treatment significantly reduced serum HA, P3NP, and laminin contents ($p<0.05$, one way ANOVA). In addition, during the six-week treatment period, in the 150 mg/kg GP-T treatment group, the serum hyaluronic acid was maintained at a constant level that is close to the level of the normal group. These results clearly show that GP can significantly reduce the increase in serum fibrosis factors in DEN induced rats. Therefore, GP extracts can be used as in vivo anti-fibrosis agents.

4-3: GP-T Inhibits DEN-Induced Liver Fibrosis

Figure 11A:
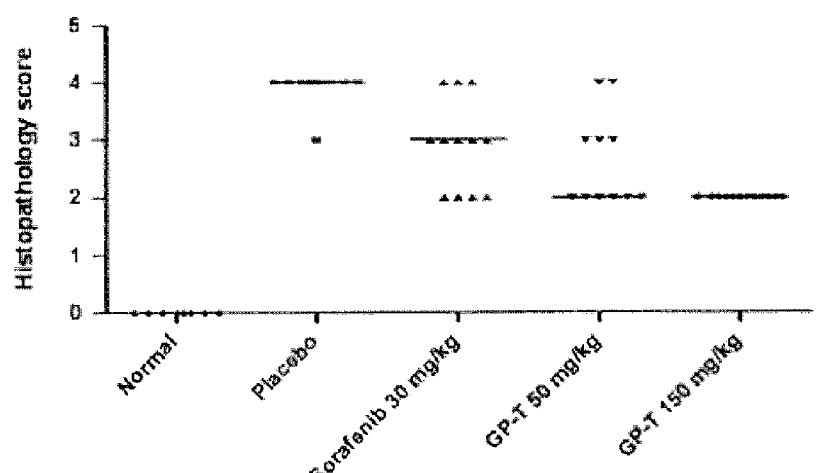
FIG. 11A shows reduction of histopathology scores by treatment with GP-T in accordance with embodiments of the invention.
Figure 11B:
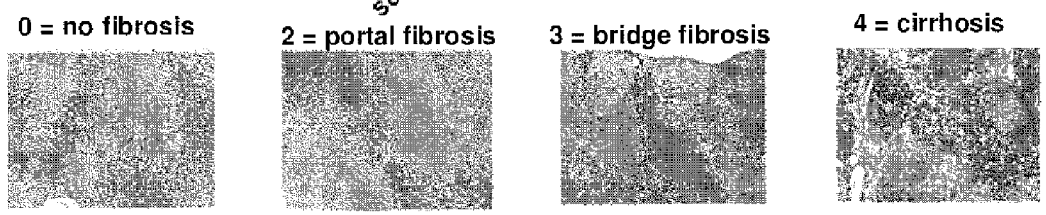
FIG. 11B shows pathological stains for various stage of the lesion.

Paraffin-embedded liver tissue section was stained with Masson's trichrome collagen staining (TRI stain) to analyze whether GP-T treatment improves DEN-induced liver fibrosis in animals. The results show that collagen fibers precipitate around the portal area and a region between the central vein and sinusoid. Based on Brunt fibrosis grading system, the severity is classified in five categories: 0=absence of fibrosis; 1=portal fibrosis; 2=fibrous portal expansion;

3=bridge fibrosis; and 4=cirrhosis (see FIG. 11B). (Hepatology, Vol 30, pp 241-246, 2000).

FIG. 11A shows the histopathology scores of the samples. FIG. 11B shows the staining images of the various stages of the pathology. As can be seen that fibrosis in the DEN-induced rats often falls in the most severe category: cirrhosis. All rats treated with GP-T show reduced extents of DEN-induced liver fibrosis in the animals, particularly the group treated with 150 mg/kg GP-T show fibrosis degrees of 2 or lower. These results indicate that GP can effectively slow or stop the progression of liver fibrosis.

4-4: GP-T Inhibits DEN-Induced Liver Astrocyte Activation

The α-SMA special immunochemistry staning of tissue section staining can be used to investigate whether GP-T treatment improves the extent of DEN-induced liver stelate cell activation. In addition, one can quantify the therapeutic effects.

Figure 12A:
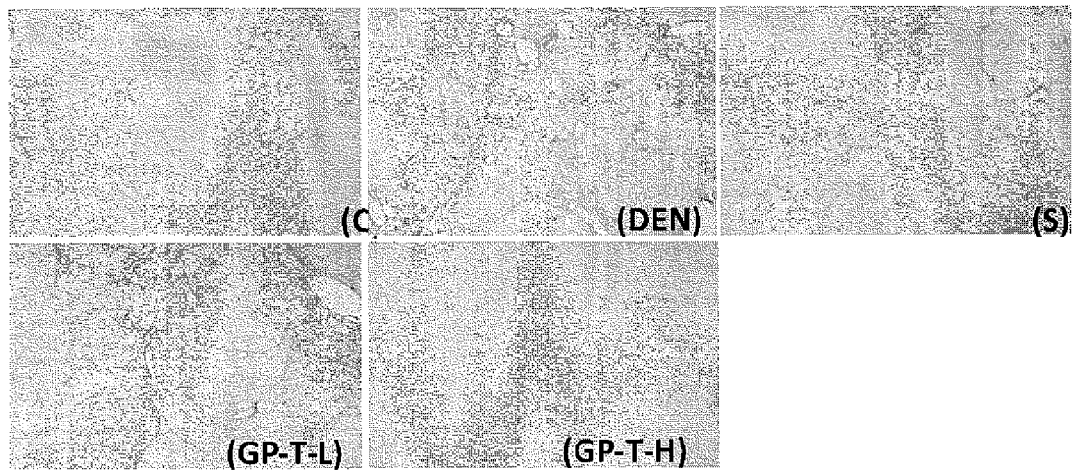
FIG. 12A shows staining of α-SMA of pathological section.

As shown in FIG. 12A, pathology study of normal rat tissue section revealed that activated astrocytes are only found around the smooth muscle of blodd vessels. In the treated rat tissue section, there are a large number of activated astrocytes discributed around the portal area and in tissues around sinusoidal space. However, in all drug treated groups, sorafenib group (S), GP-T 50 mg/kg group (GP-T-L) and GP-T 150 mg/kg group (GP-T-H), there were significantly reduced number of activated astrocytes.

Figure 12B:
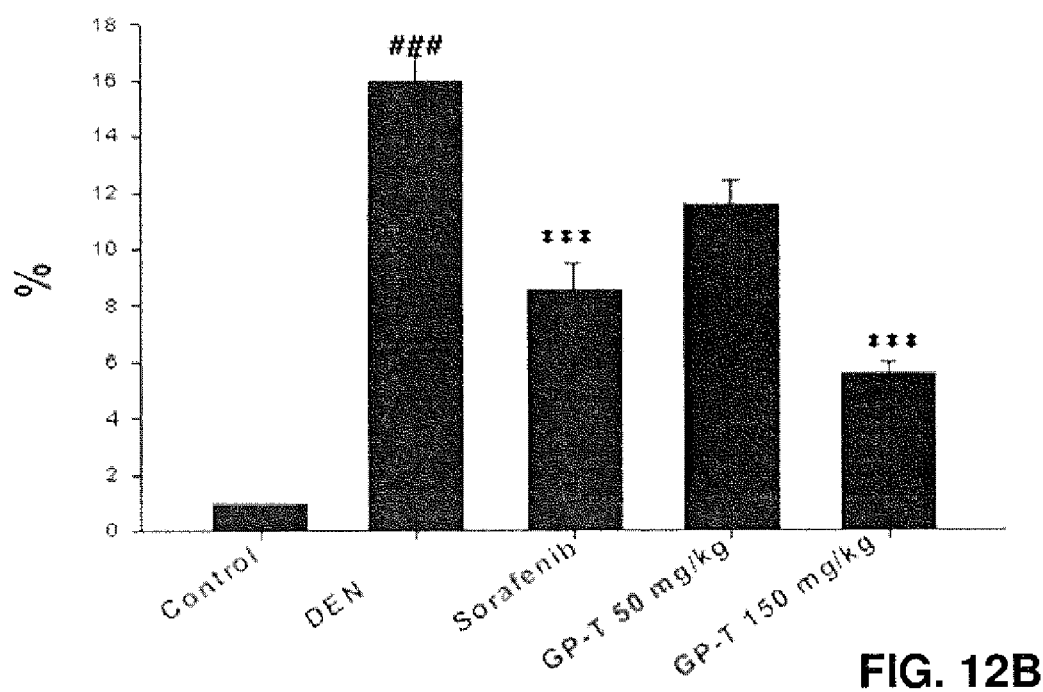
FIG. 12B quantitation of staining of α-SMA and effects of GP-T treatments.

FIG. 12B shows quantity data after treatments with various drugs. Among these, the 150 mg/kg GP-T treatment group shows particularly good results (p<0.001). These results show that GP can inhibit DEN-induced liver astrocyte activation, thereby reducing the synthesis and accumulation of collagen.

4-5: GP-T Inhibits DEN-Induced Liver Tissue Damages

Paraffin-embedded liver tissue section staining with hematoxylin and eosin can be used to study whether GP-T can improve DEN-induced liver tissue damages. Liver tissue damages can be classified into five categories: 1, 2, 3, 4, and 5, respectively, represent extremely minor, minor, medium, medium severe, and severe damages, while 0 indicates no damage at all. The results are shown as "medium" value in each group. Combined pathological examination results show that DEN-induced liver damages mainly include liver fibrosis, liver nodule recurrence, round cell hyperplasia, bile duct hyperplasia, cyst of bile duct, hepatocyte mutation, etc.

Figures 13A, 13B:
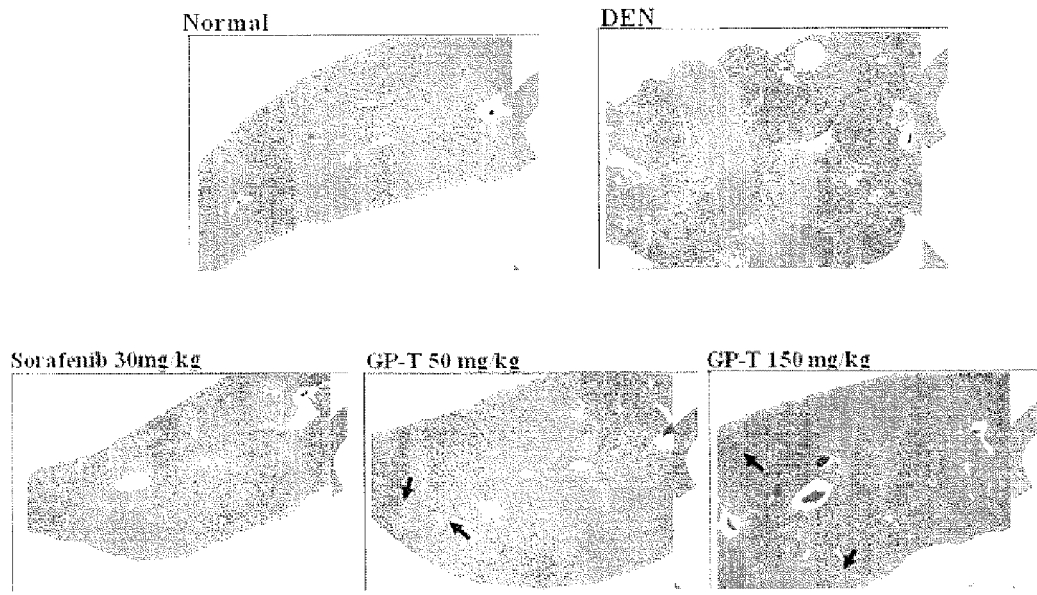
FIG. 13A shows HIE stains of pathological sections.
FIG. 13B shows summary of liver pathological symptoms for various treatment groups.

As shown in FIG. 13A, GP-T (50 mg/kg and 150 mg/kg) treatments all alleviated liver damages, particularly with the high dose, which produced the least liver damages. FIG. 13B summarizes results for the various parameters for the different treatment groups. These results show that GP is effective in improving the DEN-induced liver damages.

Example 5

Pharmaceutical Evaluation Using an Animal, in which DEN-Induced Tumor has been Removed Male five-to-six weeks old Wistar rats were obtained from the animal center at the National Taiwan University Medical School. The rats were fed drinking water containing 100 ppm carcinogen, diethylnitrosamine (DEN). During the feeding period, the rats were weighed weekly. The concentrations of DEN were increased according to the body weight increases. After continuous feeding for 9 weeks, DEN was sufficient to induce liver cirrhosis and liver cancer in rats. The liver cancers were removed by surgery after the 9 week period. Then, the rats were treated with two different doses of the test drugs (GP-T) for four weeks (from the ninth week to the thirteenth week). Some rats were given pirfenidone as positive control. In this experiments, each group has n=6-8 rats. This experiment uses a rat model, coupled with feeding the rats with different doses of the test drugs, to evaluate the impacts of the test drugs on the recurrence of liver cirrhosis and liver cancers.

Figure 14A:
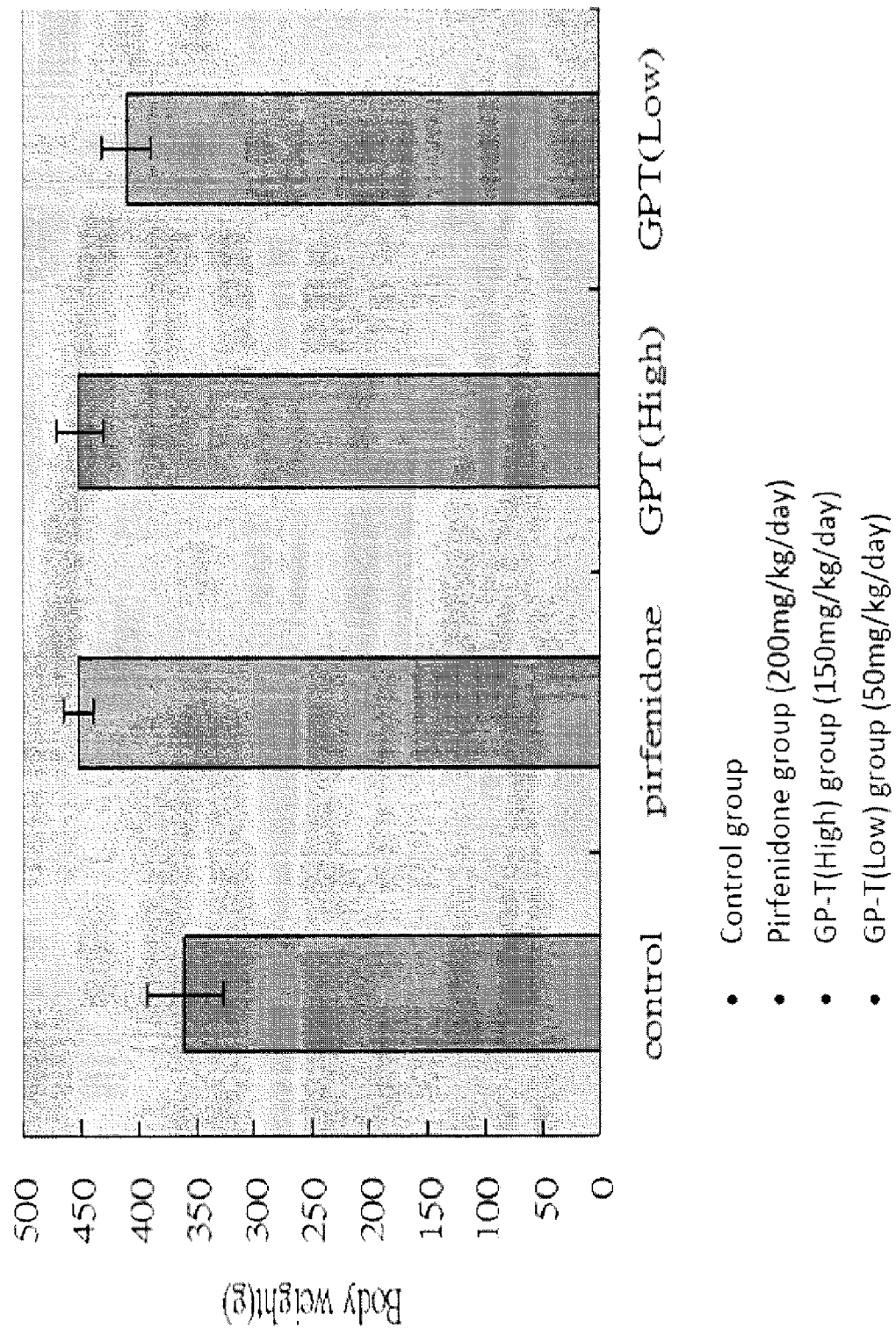
FIG. 14A body weight changes for various treatment groups.
Figure 14B:
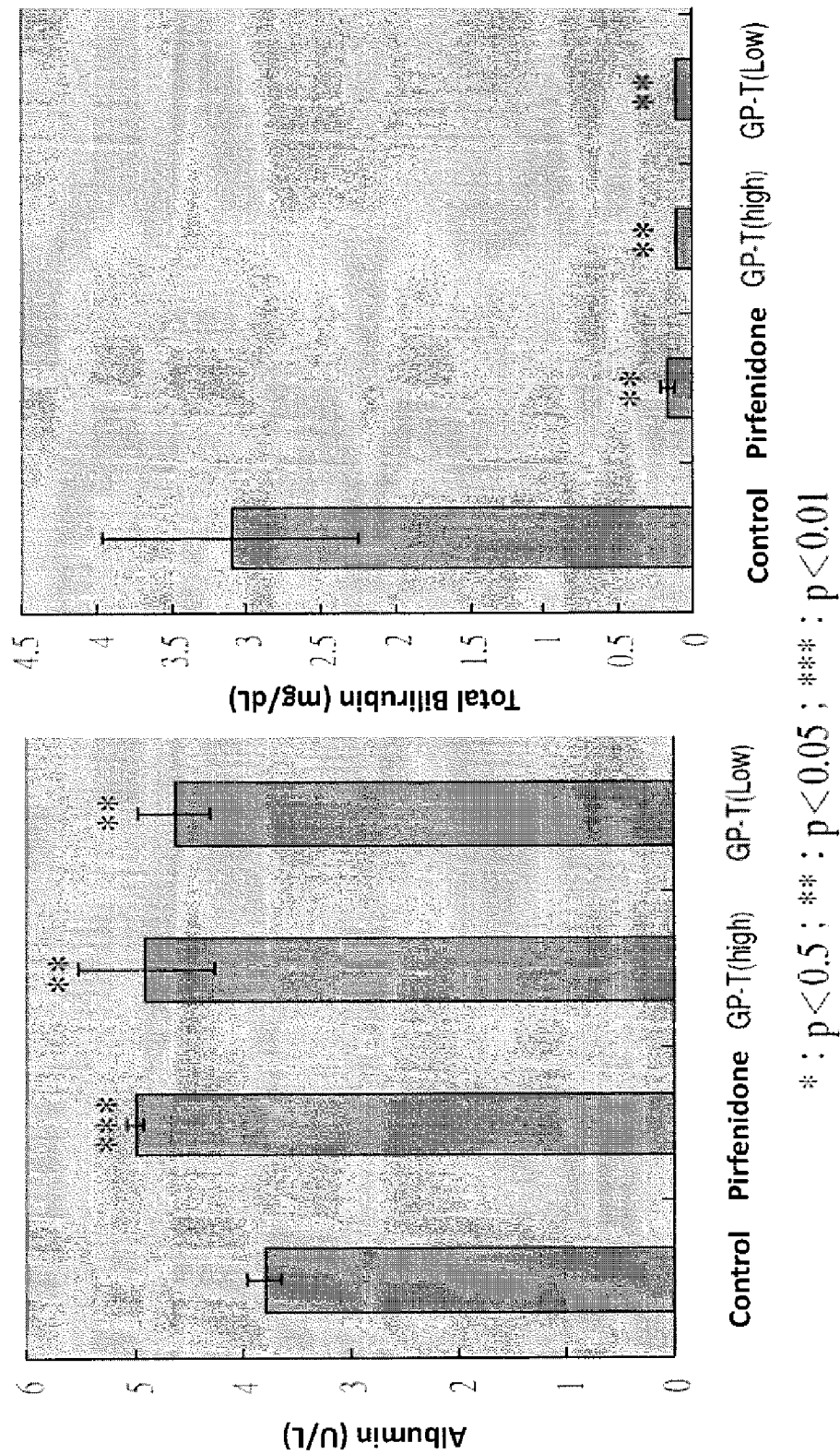
FIG. 14B shows albumin and bilirubin levels for various treatment groups.

FIG. 14A shows the body weight changes of the various groups. FIG. 14B shows the changes in albumin and bilirubin for the various groups.

After tumor ablation, the carcinogenesis presented by GST-p(+) density was decreased in pirfenidone, GP-T(H), and GP-T(L) groups. The final tumor burden was decreased in the GP-T(H) and GP-T(L) groups (FIG. 14E). However, pirfenidone showed no prophylactic effect on the recurrence of carcinogenesis after tumor removal. These results show that in the test for prevention of recurrence of liver fibrosis and liver cancers, rats treated with 50 mg/kg/day and 150 mg/kg/day showed better results than the positive control group.

Figure 14C:
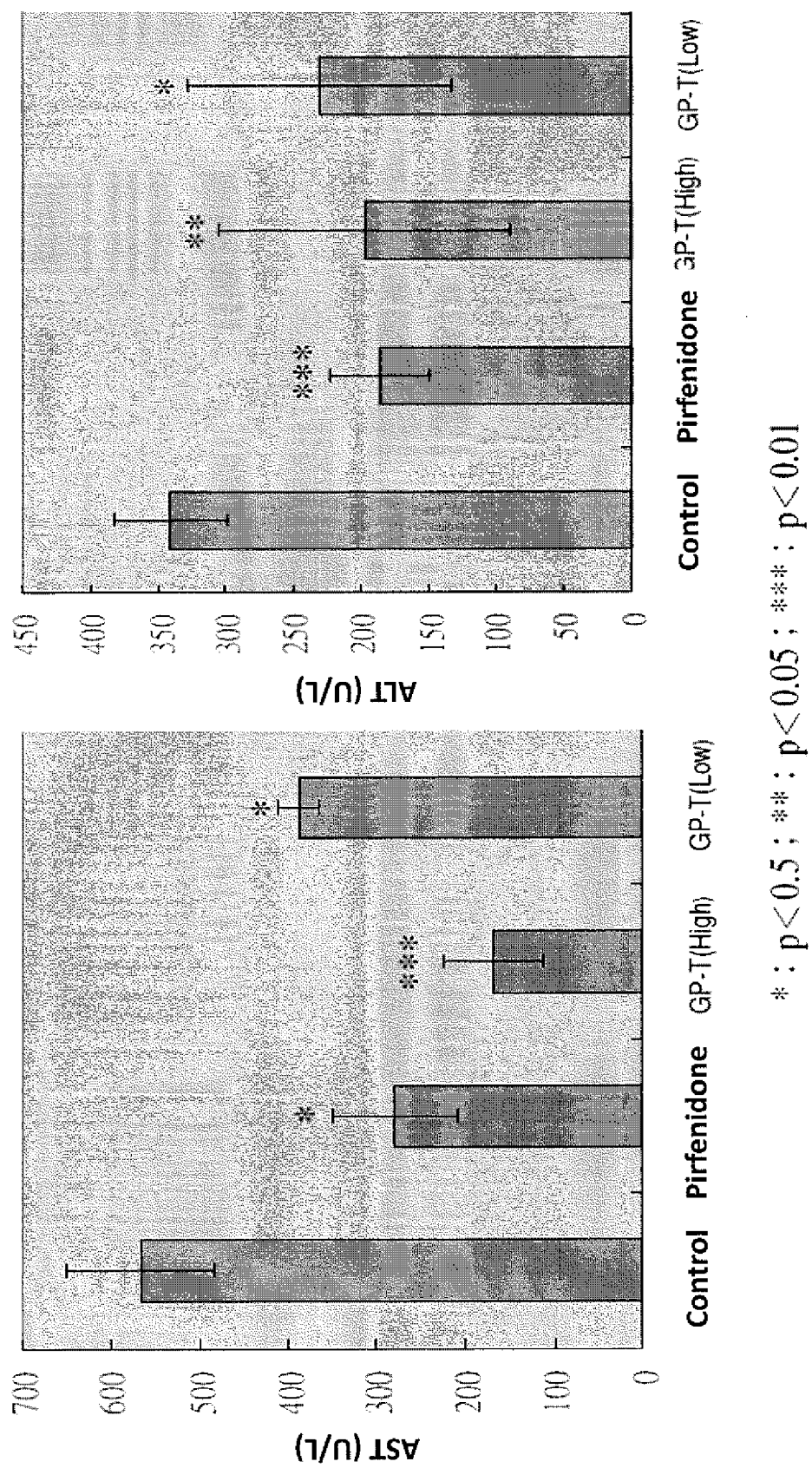
FIG. 14C shows serum liver enzyme markers for the various treatment groups.

Serum chemistry analysis of albumin, total bilirubin, aspartate aminotransferase (AST), and alanine aminotransferase (ALT) levels showed that GP treatments had liver function protective effects (FIG. 14C).

Figure 14D:
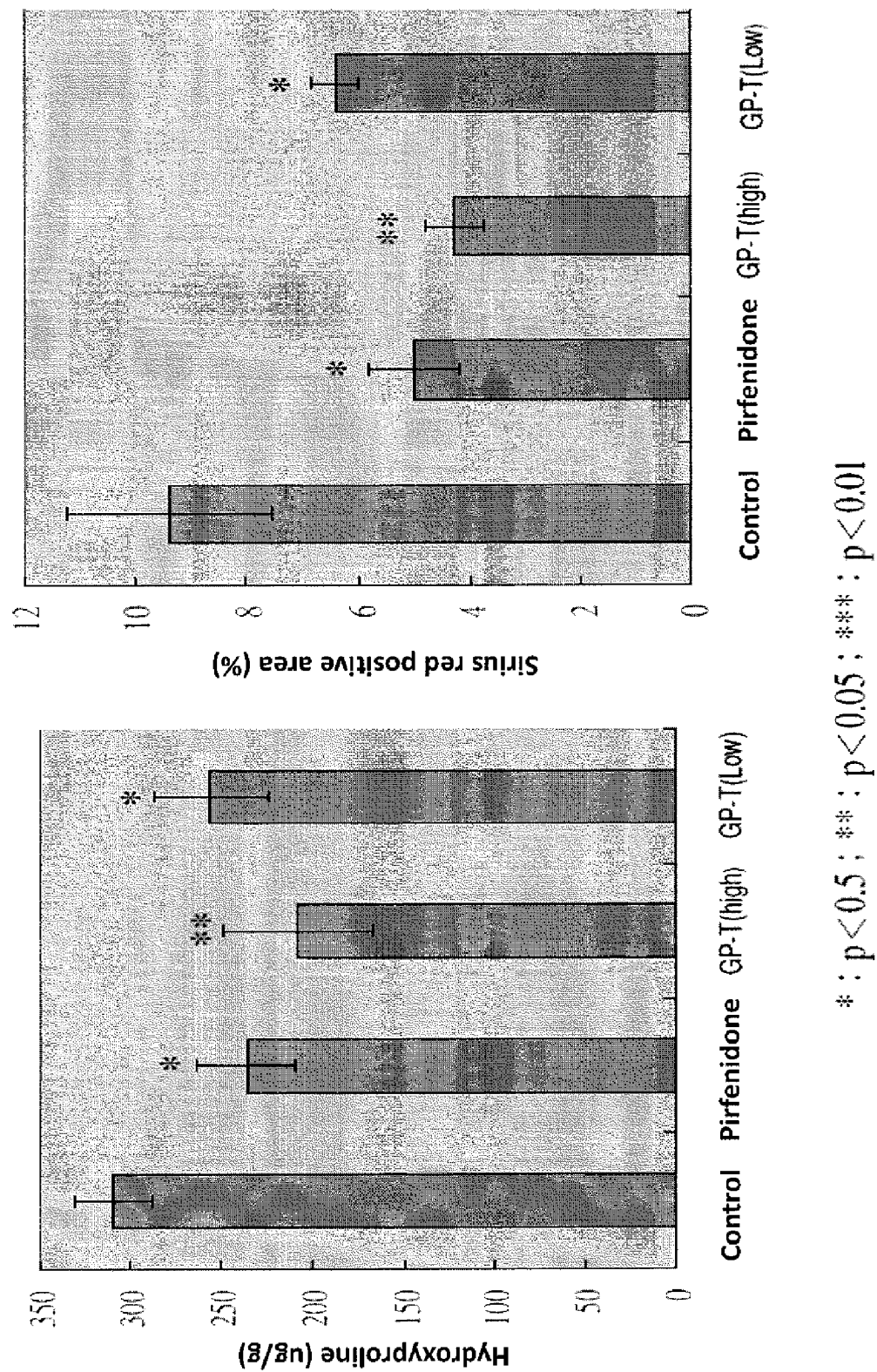
FIG. 14D shows serum fibrosis indicators for the various treatment groups.
Figure 14E:
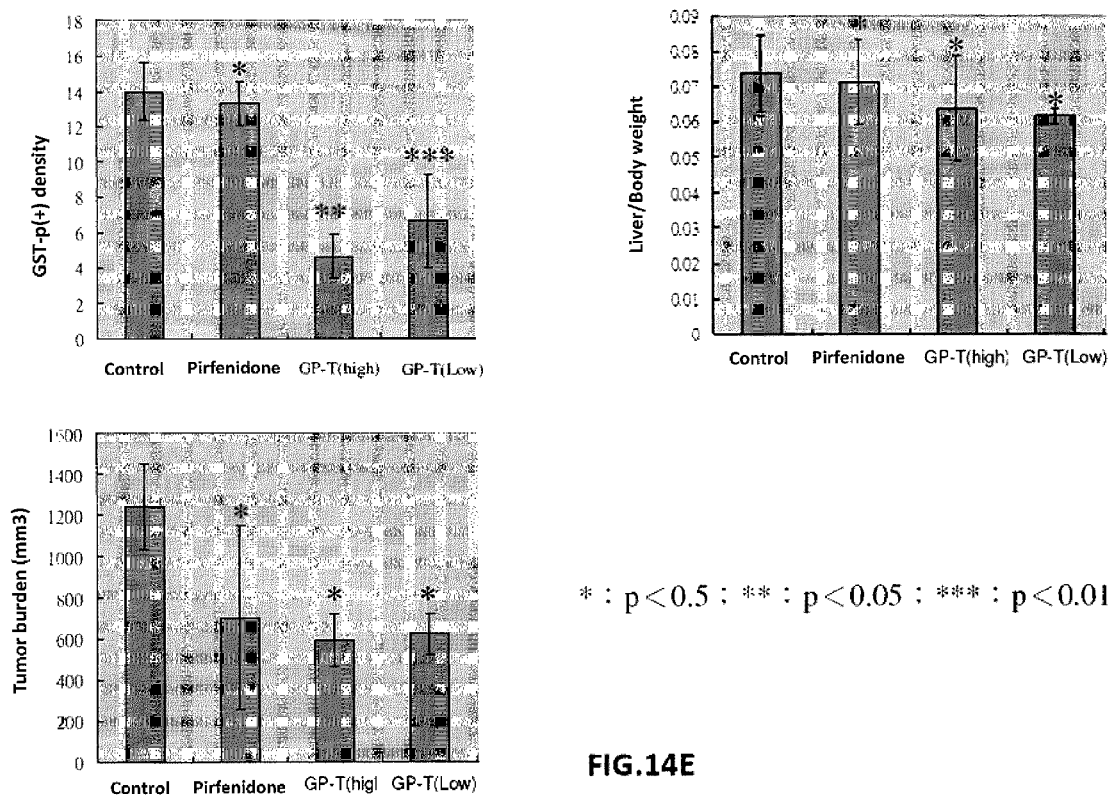
FIG. 14E shows tumor burdens for the various treatment groups.

FIG. 14D shows the fibrosis indicators for the various groups. Hydroxyproline content in liver (left panel) decreased significantly in pirfenidone, GP-T(H) and GP-T (L) groups. Sirius stain areas (right panel) were decreased significantly all treatment groups. Based on fibrosis index, the contents of hydroxyproline in liver and Sirius stain area also indicate that both GP treatment groups had significant effects in improving liver fibrosis, with the treatment with GP-T at 150 mg/kg/day showed a superior result to those of treatments with 50 mg/kg/day of GP-T and treatment with pirfenidone 200 mg/kg/day. This means that liver fibrosis was ameliorated in these groups. Based on tumorigenesis index (GST-p(+) density) and tumor burden, GP-T also showed better results than the positive control.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for preparing an extract of *Graptopetalum paraguayense*, comprising:
    extracting a *Graptopetalum paraguayense* (GP) starting material with an alcoholic solvent to produce an alcoholic extract and a residue;
    separating the residue from the alcoholic extract;
    extracting the residue with an aqueous dimethyl sulfoxide (DMSO) solvent to produce a DMSO extract;
    subjecting the DMSO extract to ultrafiltration using a filter having a selected molecular weight cutoff;
    drying a fraction retained by the filter to obtain the extract of *Graptopetalum paraguayense;*
    wherein the ultrafiltration is performed using a tangential flow filtration system;
    wherein the selected molecular w ht cutoff is about 5 kDa.
2. The method of claim 1, wherein the OP starting material is a powder of leaves of GP.
3. The method of claim 1, wherein the aqueous dimethyl sulfoxide (DMSO) solvent contains about 30% DMSO.

4. The method of claim 3, wherein the DMSO extract was diluted with water to about 10% DMSO prior to ultrafiltration.

5. The method of method 1, wherein the alcoholic solvent is methanol or ethanol.

6. The method of claim 1, further comprising filtering the DMSO extract prior to ultrafiltration.

* * * * *